(12) United States Patent
Tumlin et al.

(10) Patent No.: US 10,987,320 B2
(45) Date of Patent: Apr. 27, 2021

(54) METHODS AND COMPOSITIONS FOR PREVENTING OR TREATING CALCIPHYLAXIS

(71) Applicant: Epizon Pharma, Inc., New York, NY (US)

(72) Inventors: James A. Tumlin, Lawrenceville, GA (US); Paul L. Darke, Hingham, MA (US); John M. Rudey, New York, NY (US)

(73) Assignee: Epizon Pharma, Inc., New York, NY (US)

( * ) Notice: Subject to any disclaimer, the term of this patent is extended or adjusted under 35 U.S.C. 154(b) by 0 days.

(21) Appl. No.: 16/902,709

(22) Filed: Jun. 16, 2020

(65) Prior Publication Data

US 2020/0306208 A1 Oct. 1, 2020

Related U.S. Application Data

(62) Division of application No. 16/435,230, filed on Jun. 7, 2019, now Pat. No. 10,736,858.

(Continued)

(51) Int. Cl.
*A61K 31/122* (2006.01)
*A61K 31/047* (2006.01)
(Continued)

(52) U.S. Cl.
CPC .......... *A61K 31/122* (2013.01); *A61K 31/047* (2013.01); *A61K 31/22* (2013.01);
(Continued)

(58) Field of Classification Search
CPC .... A61K 31/047; A61K 31/122; A61K 31/22; A61K 31/366; A61K 31/40;
(Continued)

(56) References Cited

U.S. PATENT DOCUMENTS 9,012,693 B2 4/2015 Skattebol et al.
9,512,153 B2 12/2016 Moller et al.
(Continued)

FOREIGN PATENT DOCUMENTS

EP 1728507 A1 12/2006
WO WO-2008006607 A2 1/2008
(Continued)

OTHER PUBLICATIONS

Daniells (2015, pp. 1-3, downloaded from the internet on Nov. 9, 2020, URL: https://www.nutraingredients.com/Article/2015/05/20/Should-vitamin-K2-also-be-recommended-for-statin-users).*
(Continued)

*Primary Examiner* — Savitha M Rao
(74) *Attorney, Agent, or Firm* — Goodwin Procter LLP

(57) ABSTRACT

The invention provides methods and compositions for preventing or treating (e.g., slowing the progression of, arresting, and/or reversing) calciphylaxis in a subject in need thereof and, more particularly, the invention relates to methods of using menaquinone-7 (MK-7) and/or menaquinol-7 (MKH2-7) for preventing or treating calciphylaxis in a subject with one or more of the following: diabetes, chronic kidney disease, end stage renal failure, and COPD or a subject undergoing hemodialysis and/or receiving anticoagulant therapy and/or statin therapy.

25 Claims, 2 Drawing Sheets

Related U.S. Application Data

(60) Provisional application No. 62/682,794, filed on Jun. 8, 2018.

(51) Int. Cl.

| | | |
|---|---|---|
| *A61P 13/12* | (2006.01) | |
| *A61P 3/14* | (2006.01) | |
| *A61K 31/405* | (2006.01) | |
| *A61K 31/40* | (2006.01) | |
| *A61K 31/47* | (2006.01) | |
| *A61K 31/22* | (2006.01) | |
| *A61K 31/505* | (2006.01) | |
| *A61K 31/366* | (2006.01) | |

(52) U.S. Cl.
CPC ............ *A61K 31/366* (2013.01); *A61K 31/40* (2013.01); *A61K 31/405* (2013.01); *A61K 31/47* (2013.01); *A61K 31/505* (2013.01); *A61P 3/14* (2018.01); *A61P 13/12* (2018.01)

(58) Field of Classification Search
CPC .... A61K 31/405; A61K 31/47; A61K 31/505; A61P 13/12; A61P 3/14
See application file for complete search history.

(56) References Cited

U.S. PATENT DOCUMENTS

| | | |
|---|---|---|
| 10,159,787 B2 | 12/2018 | Papiorek |
| 10,688,064 B2 | 6/2020 | Tumlin et al. |
| 2005/0123603 A1 | 6/2005 | Dalland et al. |
| 2005/0176778 A1 | 8/2005 | Vermeer |
| 2015/0031651 A1 | 1/2015 | Moller et al. |
| 2016/0184254 A1 | 6/2016 | Aukrust et al. |
| 2018/0066326 A1 | 3/2018 | Bianchi et al. |
| 2018/0199610 A1 | 7/2018 | Vermeer |
| 2019/0374483 A1 | 12/2019 | Tumlin et al. |
| 2019/0374484 A1 | 12/2019 | Tumlin et al. |
| 2020/0206158 A1 | 7/2020 | Tumlin et al. |
| 2020/0206159 A1 | 7/2020 | Tumlin et al. |
| 2020/0360301 A1 | 11/2020 | Tumlin et al. |

FOREIGN PATENT DOCUMENTS

| | | |
|---|---|---|
| WO | WO-2010/034999 A1 | 4/2010 |
| WO | WO-2012059942 A2 | 5/2012 |
| WO | WO-2013128037 A1 | 9/2013 |
| WO | WO-2014/191466 A1 | 12/2014 |
| WO | WO-2016131993 A2 | 8/2016 |
| WO | WO-2019/021232 A1 | 1/2019 |

OTHER PUBLICATIONS

M. Angelis et al., Calcifylaxis in patients on hemodialysis: A prevalence study. Researchgate; Surgery, 1083-1090, 1997.
S. Bhambri et al., Calciphylaxis: A Review; Clinical aesthetic, Jul. 2008, vol. 1, No. 21.
V. M. Brandenberg et al., Lack of Evidence does not justify neglect: how can we address unmet medical need in calciphylaxis? Nephrol Dial Transplant, 2016, 0; 1-8.
M.N. Budisvljevic, Calciphylaxis in Chronic Renal Failure, Journal of the American Society of Nephrology, vol. 7, No. 7, 978-982, 1996.
H.C. Buitenhuis et al., Comparison of the vitamins K1, K2 and K3 as cofactors for the hepatic vitamin K ..Biochemica et Biphysica Acta, 1034 (1990) 170-175, Elsevier Science.
R. Caluwe et al., Vitamin K2 supplementation in haemodialysis patients: a randomized dose-finding study;Nephrol Dial Transplant (2014) 29: 1385-1390, Oxford University Press.
D. J. Card et al, Vitamin K metabolism: Current knowledge and future research; Mol. Nutr. Food Res. 2014, 58, 1590-1600; Wlleay-VCH Verlag GmBJ & Co, Weinheim.

M. Caspers et al., Two enzymes catalyze vitamin K 2,3-epoxide reductase activity i mouse: VKORC1 is highly expressed . . . Thrombosis Research, 135 (2015) 977-983. Elsevier.
M. L. L. Chatrou et al, Role of vitamin K-dependent proteins in the arterial vessel wall, Hamostaseologie Apr. 2011, 251-257.
P. Delanaye et al., Dephosphorylated-uncarboxylated Matrix Gla protein concentration is predictive of vitamin K status and is correlated with . . . , BMC Nephrology 2014, 15:145.
A. D'Ordorico et al. Quinone-induced DNA single strand breaks in human colon carcinoma cell . line; Carcinogenesis, vol. 18, No. 1, 43-46, 1997.
P. Dowd et al, The mechanism of action of vitamin K, Annu. Rev. Nutr. 1995, 15:419-440.
K. Z. Edson et al, Cytochrome P450-Dependent Catabolism of Vitamin K: w-Hydroxylation catalysed by Human CYP4F2 and CYP4F11, Biochemistry, 2013, 52(46), 8276-8285.
Bresson et al., Vitamin K added for nutritional purposes in food for particular for nutritional uses, food supplement and foods intended for the general population, Scientific Opinion, The EFSA, 822, 1-31.
N. Emaus et al., Vitamin K2 supplementation does not influence bone loss in early menopausal women: a randomized . . . , Osteoporosis Int. 2010, 21, 1731-1740.
L. Forli et al., Dietary vitamin K2 Supplement improve bone status after lung and heart transplantation; Transplantation, vol. 89, No. 4, 458-464.
C. G. M. Gast et al, A high menaquinone intake reduces the incidence of coronary heart disease, Nutrition, Metabolism & Cardiovascular Diseases, 2008, 1-7, Elsevier.
J. Himmelfarb, Plasma protein thiol oxidation and carbonyl formation in chronic renal failure, Kidney International, vol. 58, 2000, 2571-2578.
R. M. Holden et al, Vitamin K and D Status i Stages 3-5 Chronic Kidney Disease, Clin. K. Am. SO Nephrol, 5, 590-597, 2010.
D. Hollander et al, Vitamin K2 absorption by rat everted small intestinal sacs, American Journal of Physiology, vol. 231, No. 2, 1976, 415-419.
D. Hollander, Vitamin K2 colonic and ileal in vivo absorption: . . . , Vitamin K2 Absorption in vivo, E124-E130, 1997.
T. Inoue et al. Randomized controlled study on the prevention of osteoporotic fractures, Journal of Bone and Mineral Metabolism, 2009, 27, 66-75.
Y. Ishida et al., Comparative Efficacy of Hormone Replacement Therapy . . . , Am. J. Med, 2004, 117, 549-555; Elsevier, Inc.
J. Iuwamoto et al, Effect of combined administration of vitamin D3 and K2 on bone mineral density . . . , J. Orthop. Sci, 2000, 5; 546-551.
D. T. Janigan, Calcified Subcutaneous Arterioles with infarcts of the subcutis and skin . . . , American Journ. of Kidney Diseases, vol. 35, No. 4, 2000, 588-597.
M. Kaneki et al., Japanese fermented soybean food as the Major Determinant of the large Geographic Difference . . . . Nutrition, 2001, 17: 315-321, Elsevier Science.
M.H.J. Knapen, Vitamin K2 supplementation improves hip bone geometry . . . , Osteoporosis Int. 2007, 18, 963-972.
M.H.J. Knapen, Three-year-dose menaquinone-7 supplementation helps decrease bone loss . . . , Osteoporosis Int. 2013, 24, 2499-2507.
I. Kurnatowska et al., Effect of vitamin K2 on progression of atherosclerosis and vascular calcification in nondialyzed patients with chronic kidney disease stage 3-5, Polskie Archiwum Medycyny Wewnetrznej, 2015, Online, 631-40.
N. New, Calcific Uremic Arteriolopathy in Peritoneal Dialysis Population, Intern. J. Nephrology, vol. 2011, Article ID 982854, 9 pages.
S. U. Nigwekar et al., A National Representative Study of Calcific Uremic Arteriolopathy Risk Factors, J Am Soc Nephrol, Clinical Research, 27, 2016, 3421-3429.
S. U. Nigwekar et al., Quantifying a rare disease in administrative data: the example of calciphylaxis, JGIM Online, Jul. 17, 2014, S924-S931.
R. U. Pliquett et al., Calciphylaxis in chronic, non-dialysis-dependent renal disease, BMC Nephrology, 2003, 4:8.

(56) References Cited

OTHER PUBLICATIONS

P.A. Price et al., Conserved phosphorylation of serines in the Ser-X-Glu/Ser(PP) sequences of the vitamin K-dependent matrix Gla . . . Protein Science, 1994, 3:822-830.
Y. Purwosunu et al, Vitamin K2 treatment for postmenopausal osteoporosis in Indonesia, Journal of Obstet and Gynaecol Res, vol. 32, No. 2, 230-234, 2006.
M.A. Rishavy et al, Novel Insight into the Mechanism of the Vitamin K Oxidoreductase (VKOR), The Journal of Biological Chemistry, vol. 286, No. 9, 7267-7278, 2011.
T. Sato et al., Comparison of menaquinone-4 and menaquinone-7 bioavailability in healthy women, Nutrition Journal, 2012, 11:93.
L. J. Schurgers et al., Differential lipoprotein transport pathways of K-vitamins in healthy subjects, Biochimica et Biophysica Acta 1570 (2002) 27-32.
L. J. Schurgers et al., Vitamin K-containing dietary supplements: comparison of synthetic vitamin K1 . . . Blood, 2007, 109: 3279-3283.
L. J. Schurgers et al., Regression of warfarin-induced medial elastocalcinosis by high intake of vitamin K in rats, Blood, 2007, 109:2823-2831.
M.J. Shearer et al., Metabolism and cell biology of vitamin K, Thromb Haemost 2008, 100:530-547.
M.J. Shearer et al., Vitamin K Nutrition, Metabolism, and Requirements: Current Concepts and Future Research, Adv. Nutr. 3:182-195, 2012.
M.J. Shearer et al., Recent trends in the metabolism and cell biology of vitamin K with special reference to . . . J. Lipids Res., 2014, 55:345-362.
M. Shiraki et al, Vitamin K2 (Menatetrenone) Effectively Prevents Fractures and Sustains Lumbar Bome Mineral . . . , Journ. of Bone and Mineral Research, 2000, 15:515-521.
A. Siltari et al., Effects of Vitamin K-1 and Menaquinone-7 on Vascular Function and Blood Pressure . . . , Pharmacology & Pharmacy, 2014, 5, 1095-1105.
K. M. Sowers et al, Calcific Uremic arteriolopathy, Oxidative Medicine and Cellular Longevity, 3:2, 109-212, 2010.
T. Ushiroyama et al, Effect of Continuous combined therapy with vitamin K2 and vitamin D3 on bone mineral density . . . , Maturitas 41 (2002) 211-221.
C. Vermeer, Vitamin K: the effect on health beyond coagulation—an overview, Food & Nutrition Research, 2012, 56:5329.
L. E. T. Vissers et al, Intake Dietary Phylloquinone and Menaquinones and Risk of Stroke, J. Am. Heart Assoc. 2013, 2:e000455.
L. M. Vossen et al, Menaquinone-7 Supplementation to Reduce Vascular Calcification in Patients with Coronary Artery Disease . . . , Nutrients, 2015, 7, 8905-8915.
B. Walther et al., Menaquinones, Bacteria and the Food Supply: The Relevance of Dairy and Fermented Food Products . . . , Adv. Butr. 4: 463-473, 2013.
R. Westenfeld et al, Effect of Vitamin K2 Supplementation on Functional Vitamin K Deficiency . . . , Am. J. Kidney Dis. 59(2): 186-195, 2012.
W. A. Wilmer et al, Caciphylaxis: Emerging Concepts in Prevention, Diagnosis and Treatment, Seminarsin. dialysis, vol. 15, No. 3, 2002, pp. 172-186.
U. Wollina, Update on Cutaneous Calciphylaxis, Indian J. Dermatol, 2013, 58(2): 87-92.
A. S. Yalin et al, Calciphylaxis: A Report of Six Cases and Review of Literature, Renal Failure, 2013, 35(1): 163-169.
S. Scheiber et al., High-Dose Menaquinone-7 Supplementation Reduces Cardiovascular Calcification in a Murine Model of Extraosseous Calcification; Nutrients 2015, 7, 6991-7011.
Y. Li et al., Effect of Vitamin K2 on Type 2 diabetes mellitus: A review; Diabetes Research and Clinical Practice, 136, 2018, 39-51.
C. Qiu et al., Vitamin K2 inhibits rat vascular smooth muscle cell calcification by restoring . . . , Molecular Cell Biochem., 2017, 433: 149-159.
L. Kovell, Lipid management guidelines for adults with chronic kidney disease; American College of Cardiology, Expert Analysis, 2016.
S. Hughes et al., Anticoagulation in chronic kidney disease patients—the practical aspects; Clin. Kidney J., 2014, 7:442-449.
Levy (2007) "Potential treatment of calciphylaxis with vitamin K2: Comment on the article by Jacobs-Kosmin and DeHoratius," Arthritis Care & Research 57(8): 1575-1576.
Riegert-Johnson et al. (2001) "Calciphylaxis associated with cholangiocarcinoma treated with low-molecular-weight heparin and vitamin K," Mayo Clin Proc. 76(7):749-52.
Gheduzzi, D. et al. "Matrix Gia protein is involved in elastic fiber calcification in the dermis of pseudoxanthoma elasticum patients" Laboratory Investigation (2007) vol. 87, pp. 998 to 1008.
Vik, A.B. "Vitamin K2 and arterial calcification" Agro Food Industry Hi-Tech (2008) vol. 19 No. 6, pp. 9 to 13.
Written Opinion of the International Searching Authority in PCT/US2019/036139, dated Aug. 14, 2019, 7 pages.
International Search Report in PCT/US2019/036139, dated Aug. 14, 2019, 4 pages.
Written Opinion of the International Searching Authority in PCT/US2019/036138, dated Aug. 14, 2019, 5 pages.
International Search Report in PCT/US2019/036138, dated Aug. 14, 2019, 4 pages.
Pross et al. "Rat and human aortic smooth muscle cells display differing migration and matrix metalloproteinase activities in response to dexamethasone" (2002) J. Vascl. Surg. 35; 1253-1259.
U.S. Appl. No. 16/435,230, Methods and Compositions for Preventing or Treating Calciphylaxis, filed Jun. 7, 2019.
U.S. Appl. No. 16/902,701, Methods and Compositions for Preventing or Treating Calciphylaxis, filed Jun. 16, 2020.
U.S. Appl. No. 16/902,705, Methods and Compositions for Preventing or Treating Calciphylaxis, filed Jun. 16, 2020.
U.S. Appl. No. 16/435,241 U.S. Pat. No. 10,688,064, Methods and Compositions for Preventing or Treating Tissue Calcification, filed Jun. 7, 2019.
U.S. Appl. No. 16/817,347, Methods and Compositions for Preventing or Treating Calciphylaxis, filed Mar. 12, 2020.
U.S. Appl. No. 16/817,363, Methods and Compositions for Preventing or Treating Calciphylaxis, filed Mar. 12, 2020.
U.S. Appl. No. 16/817,374, Methods and Compositions for Preventing or Treating Calciphylaxis, filed Mar. 12, 2020.

* cited by examiner

METHODS AND COMPOSITIONS FOR PREVENTING OR TREATING CALCIPHYLAXIS

CROSS REFERENCE TO RELATED APPLICATIONS

This application is a divisional of U.S. patent application Ser. No. 16/435,230 filed on Jun. 7, 2019, which claims priority to and the benefit of U.S. Provisional Application No. 62/682,794, filed on Jun. 8, 2018, the contents of each of which are incorporated herein by reference in their entirety.

FIELD OF THE INVENTION

The invention relates generally to methods and compositions for preventing or treating (e.g., slowing the progression of, arresting, and/or reversing) calciphylaxis in a subject in need thereof and, more particularly, the invention relates to methods of using menaquinone-7 (MK-7) and/or menaquinol-7 (MKH2-7), for preventing or treating (e.g., slowing the progression of, arresting, and/or reversing) calciphylaxis in a subject with diabetes, chronic kidney disease, end stage renal disease, or a subject undergoing hemodialysis and/or receiving anticoagulant therapy and/or a subject who has been, or is presently, on statin therapy and/or suffering from chronic obstructive pulmonary disorder (COPD).

BACKGROUND

Under normal physiological conditions, plasma calcium and phosphate are present at concentrations close to supersaturation levels and, as a result, may be expected to precipitate in soft tissue (e.g., blood vessels) as crystalline hydroxyapatite. The observation that this process does not occur in healthy subjects suggested the presence of potent chemical and biologic means for blocking pathologic calcification (Price, et al. (2002) "Discovery of a High Molecular Weight Complex of Calcium, Phosphate, Fetuin, and Matrix-Carboxyglutamic Acid Protein in the Serum of Etidronate-treated Rats," JOURNAL BIOL. CHEM. 277 (6): 3926-3934).

When the suppression of calcification is disrupted, such as in subjects with diabetes and chronic kidney disease (CKD), pathologic calcification of soft tissue (e.g., blood vessels) can occur. It is understood that diabetes can lead to CKD and end stage renal disease (ESRD), which is characterized by uremia. Uremia can promote the oxidation of Vitamin K hydroquinone (KH2), thereby disrupting the cyclic regeneration of Vitamin K, among other effects. (See, FIG. 1.) In addition, certain treatments can cause or contribute to Vitamin K dysregulation, including warfarin-based anticoagulant therapy and statin therapy. The loss of functional Vitamin K results in the loss of important regulators of mineralization, leading to pathologic calcification of tissue. In the case of arterial calcification, intradermal microvascular thrombosis is observed to occur, resulting in small vessel blockages and surrounding tissue death.

Calciphylaxis (also referred to as Calcific Uremic Arteriolopathy (CUA)), is a rare, but potentially fatal complication of chronic kidney disease (CKD), predominantly affecting patients with end-stage renal disease (ESRD) on hemodialysis. The condition is characterized by calcification of subcutaneous arterioles and infarctions of the adjacent subcutis and skin (Janigan et al. (2000) "Calcified subcutaneous arterioles with infarcts of the subcutis and skin ("calciphylaxis") in chronic renal failure," AMERICAN JOURNAL OF KIDNEY DISEASES 35(4):588-97; Brandenburg et al. (2016) "ERA-EDTA Working Group on CKD-MBD and EUCAL-NET. Lack of evidence does not justify neglect: how can we address unmet medical needs in calciphylaxis?" NEPHROL DIAL TRANSPLANT. 31(8):1211-9; Brandenburg et al. (2017) "Calcific uraemic arteriolopathy (calciphylaxis): data from a large nationwide registry," NEPHROL DIAL TRANSPLANT. 32(1): 126-132).

The exact incidence and prevalence of calciphylaxis are unknown (Brandenburg et al. 2017, supra). The estimated annual incidence is <1% and the prevalence is about 4% among chronic hemodialysis patients (Angelis et al. (1997) "Calciphylaxis in patients on hemodialysis: A prevalence study," SURGERY 122(6):1083-90; Brandenburg et al. (2014) "Calcific uraemic arteriolopathy: a rare disease with a potentially high impact on chronic kidney disease-mineral and bone disorder," PEDIATR NEPHROL. 29(12):2289-98; Brandenburg et al. (2016), supra).

Based on the United States Renal Data System, between 2010 and 2015, there was an increase in the: (i) incident number of ESRD cases from 115,829 to 124,114, respectively; (ii) prevalent counts of reported ESRD from 592,656 to 703,243, respectively; (iii) incident count of hemodialysis from 112,804 to 120,972, respectively; and point prevalent counts for hemodialysis from 414,503 to 495,433 (USRDS 2017). Assuming a <1% incidence and approximately 4% prevalence of calciphylaxis among patients on hemodialysis, the estimated annual incident and prevalent counts for calciphylaxis are around 1200 and 19,800, respectively. Further, according to Mayo Clinic statistics, these numbers represent about 60% of the total U.S. calciphylaxis patient population. The other 40% is attributable to CKD patients not on dialysis, which would set the total population as of January 2018 at approximately 40,000.

Calciphylaxis is associated with significant morbidity and mortality (Mazhar et al. (2001) "Risk factors and mortality associated with calciphylaxis in end-stage renal disease, KIDNEY INT. 60(1):324-332; Wilmer et al. (2002) "Emerging Concepts in Prevention, Diagnosis, and Treatment," SEMIN DIAL. 15(3):172-86; Bhambri et al. (2008) "Calciphylaxis: a review" JOURNAL OF CLINICAL AND AESTHETIC DERMATOLOGY 1(2):38-41; Brandenburg et al. (2014), supra; Brandenburg et al. 2016, supra), resulting in a median survival of 1.5 years (Weenig et al. (2007) "Calciphylaxis: natural history, risk factor analysis, and outcome," J AM ACAD DERMATOL 56:569-579; Brandenburg et al. (2014), supra). The development of calciphylaxis may be viewed as a two-stage process, starting with the development of vascular lesions, followed by tissue ischemia secondary to the vascular lesions. Given that by the time the clinical entity becomes apparent, it is often too late to reverse the vasculopathy, the prognosis of calciphylaxis is generally poor (Wilmer et al. (2002), supra). The painful skin ulcers and tissue necrosis (the hallmarks of calciphylaxis) can lead to serious, and even life-threatening or fatal infections, contributing to an overall mortality of up to 80% (Bhambri et al. (2008), supra; Magro et al. (2011) "Calciphylaxis: a review," J AM COL CERTIF WOUND SPEC. 2(4):66-72; Brandenburg et al. (2016), supra), with more than 50% of patients dying within one year of diagnosis (Mazhar et al. (2001), supra; Bhambri et al. (2008), supra). Apart from death due to sepsis from infected, necrotic skin lesions, fatal internal organ failure has also been reported in patients with calciphylaxis (Wilmer et al., (2002), supra). In patients with ESRD on hemodialysis, calciphylaxis was found to independently increase the risk of death by eightfold, and the overall 1- and 5-year survival rates have been estimated at 45% and 35%, respectively (Mazhar et al. (2001), supra).

Several in vitro, in vivo and human cohort studies have suggested that the use of vitamin K antagonists (VKAs) such as warfarin accelerates cardiovascular calcification (Schurgers et al. (2007a) "Post-translational modifications regulate matrix Gla protein function: importance for inhibition of vascular smooth muscle cell calcification," J THROMB HAEMOST 5:2503-2511; Schurgers et al. (2007b) "Regression of warfarin-induced medial elastocalcinosis by high intake of vitamin K in rats," BLOOD 109:2823-283; Kruger et al. (2013) "Warfarin induces cardiovascular damage in mice," ARTERIOSCLER THROMB VASC BIOL 33: 2618-2624) and is a prominent risk for calciphylaxis (Hayashi et al. (2012) "A case-control study of calciphylaxis in Japanese end-stage renal disease patients," NEPHROL DIAL TRANSPLANT 27:1580-1584; Nigwekar et al. (2013) "Statin use and calcific uremic arteriolopathy: a matched case-control study," AM J NEPHROL 37:325-332; Brandenburg et al. (2016), supra).

In a study evaluating the risk factors for calciphylaxis in hemodialysis patients, 1030 hemodialysis patients with newly diagnosed calciphylaxis were matched with 2060 controls. Median duration between hemodialysis initiation and subsequent calciphylaxis development was 925 days (interquartile range [IQR], 273-2185 days). In multivariable conditional logistic regression analyses, diabetes mellitus; higher body mass index; higher levels of serum calcium, phosphorous, and parathyroid hormone; and nutritional vitamin D, cinacalcet, and warfarin treatments were associated with increased odds of subsequent calciphylaxis development (Nigwekar et al. (2016) "A Nationally Representative Study of Calcific Uremic Arteriolopathy Risk Factors," J. AM. SOC. NEPHROL. 27(11):3421-9).

Skin necrosis observed in patients with calciphylaxis appears to be due to extensive small vessel calcification and calcium accumulation in soft tissue. The mechanisms for soft tissue calcification are not completely understood; however, carboxylated MGP is considered to play an important role as a potent inhibitor of vascular calcification (Schurgers et al. (2007a), supra; Brandenburg et al. (2016), supra; Nigwekar et al. (2016), supra).

Vitamin K is an essential enzymatic co-factor that is required for post-translational modifications of Vitamin K-dependent (VKD) proteins. A number of VKD proteins are clinically relevant to CKD and ESRD patients, and include, for example, central coagulation factors such as factors II, VII, IX, and X and intercellular matrix proteins such as Matrix Gla Protein (MGP) activated protein C and osteocalcin. Vitamin K is a group of fat soluble vitamins, which include, among other things, vitamin $K_1$ (also known as phylloquinone), which is made by plants, and vitamin $K_2$ (also known as menaquinone), which is made by bacteria in gut flora. It is understood that the isoprenoid chain in vitamin $K_2$ can contain from 4 to 12 repeating isoprenoid units. For example, menaquinone-4 (or MK-4) contains four isoprenoid units whereas menaquinone-7 (or MK-7) contains seven isoprenoid units.

With regard to menaquinone-7 (MK-7), under normal conditions MK-7 is reduced to menaquinol-7 (MKH2-7) (a form of Vitamin K hydroquinone) by an NADPH-dependent reductase enzyme or enzymes (e.g., quinone oxidoreductase). Only the reduced form of MK-7 (namely MKH2-7) functions as a co-factor for the enzyme gamma glutamate carboxylase (GGCX), which catalyzes the carboxylation of Vitamin K-dependent proteins. (See, FIGS. 1 and 2.) The enzymatic carboxylation of glutamate residues results in oxidation of MKH2-7 to a 2,3-epoxide form (MK-7 2,3-epoxide). The final step of the Vitamin K cycle requires the enzymatic reduction of Vitamin MK-7 2,3-epoxide back to MK-7 by Vitamin K epoxide reductase complex subunit 1 (VKORC1, also referred to as VKOR. In some tissues, the paralog VKORC1L1 (VKORC1-Like-1) may also perform this catalytic reaction. It is known that warfarin blocks both the generation of MKH2-7, the active form of Vitamin $K_2$, as well as the regeneration of MK-7 from Vitamin MK-7 2,3-epoxide, which may lead to the higher incidence of calcification seen among patients receiving warfarin therapy.

Despite efforts to date, there is a need for new clinical approaches to prevent and/or treat calciphylaxis. In particular, there is a need for new clinical approaches to prevent and/or treat calciphylaxis in subjects with diabetes, CKD, ESRD, and subjects receiving anticoagulant and/or statin therapy.

SUMMARY OF THE INVENTION

It has been discovered that menaquinone-7 (MK-7) and/or menaquinol-7 (MKH2-7), can be used effectively at high doses, e.g., in doses of at least 2 mg per day, to prevent or treat (e.g., slow the progression of, arrest, and/or reverse) calciphylaxis in a subject, e.g., a subject with diabetes and/or chronic kidney disease.

In one aspect, the disclosure relates to a method of preventing or treating (e.g., slowing the progression of, arresting, and/or reversing) calciphylaxis in a subject in need thereof. The method includes administering to the subject an effective amount of a composition comprising substantially pure menaquinone-7 (MK-7) and/or menaquinol-7 (MKH2-7) thereby to prevent or treat the calciphylaxis. In certain embodiments, the subject has distal calciphylaxis and/or central calciphylaxis.

In another aspect, invention provides a method of preventing or treating (e.g., slowing the progression of, arresting, and/or reversing) one or more symptoms of chronic obstructive pulmonary disease (COPD) in a subject in need thereof, the method comprising administering to the subject at least 2 mg of substantially pure menaquinone-7 (MK-7) and/or menaquinol-7 (MKH2-7) per day, thereby to prevent or treat (e.g., slow the progression of, arrest, and/or reverse) the one or more symptoms of COPD, wherein the MK-7 and/or MKH2-7 is administered in a pharmaceutical composition. In certain embodiments, the one or more symptoms is selected from the group consisting of breathing difficulty, cough, mucus production, wheezing, and elastinolysis.

In another aspect, the invention provides a disclosure of a method for preventing or treating (e.g., slowing the progression of, arresting, and/or reversing) tissue calcification in a subject with calciphylaxis, wherein the subject is taking calcium-based phosphate binders and/or vitamin D analogs. The method can include administering to the subject at least 2 mg of substantially pure menaquinone-7 (MK-7) and/or menaquinol-7 (MKH2-7) per day. In certain embodiments, the subject has hyperparathyroidism.

In certain embodiments, the pharmaceutical composition comprises MK-7. In certain embodiments, the pharmaceutical composition comprises MKH2-7. In certain embodiments, the pharmaceutical composition comprises a combination of MK-7 and MKH2-7.

In certain embodiments of any of the above aspects, the subject has been diagnosed as pre-diabetic or has diabetes, e.g., type II diabetes. In certain embodiments, the subject has chronic kidney disease, e.g., stage 3, stage 4, or stage 5. In certain embodiments, the subject has COPD. In certain embodiments, the subject is undergoing hemodialysis. In certain embodiments, the subject is receiving non-warfarin-based anticoagulant therapy, such as an oral anti-coagulation therapy. In certain embodiments, if non-warfarin-based anti-coagulation therapy is used, the anti-coagulation therapy can comprise an inhibitor of Factor Xa activity (e.g., apixaban, rivaroxaban, betrixaban, edoxaban, or fondaparinux) or Factor IIa activity (e.g., dabigratran or argatroban). In certain embodiments, the subject has previously been exposed to warfarin-based anti-coagulation therapy.

In certain embodiments, the subject has a calciphylaxis-related dermal lesion. In certain embodiments, administration of the composition reduces the size of the dermal lesion, for example, administration of the composition reduces the total surface area of the dermal lesion by at least 5%, 10%, 15%, 20%, 25%, 30%, 35%, 40%, 45% 50%, 55%, 60%, 65%, 70%, 75%, 80%, 85%, 90%, 95%, or 100%.

In certain embodiments of any of the above aspects, administration of the MK-7 and/or MKH2-7 to the subject increases the subject's serum T50 value (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the subject's serum T50 value prior to administration of the respective MK-7 and/or MKH2-7.

In certain embodiments of any of the above aspects, administration of the MK-7 and/or MKH2-7 increases a ratio of a carboxylated to a non-carboxylated Vitamin K-dependent protein in the subject's plasma (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the ratio prior to administration of the respective MK-7 and/or MKH2-7. In certain embodiments of any of the above aspects, administration of the MK-7 and/or MKH2-7 decreases the amount of a non-carboxylated Vitamin K-dependent protein in the subject's plasma (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the amount prior to administration of the respective MK-7 and/or MKH2-7. In certain embodiments, the Vitamin K-dependent protein is selected from Matrix Gla Protein (MGP), Growth Arrest Specific Gene 6 (Gas-6) protein, PIVKA-II protein, osteocalcin, activated Protein C, activated Protein S, factor II, factor VII, factor IX, and factor X.

In certain embodiments of any of the above aspects, administration of the MK-7 and/or MKH2-7 increases the plasma level of osteoprotegerin or Fetuin A (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the plasma concentration of osteoprotegerin or Fetuin A prior to administration of the respective MK-7 and/or MKH2-7.

In certain embodiments of any of the above aspects, administration of the MK-7 and/or MKH2-7 decreases the plasma level of D-Dimer or Highly Sensitive C Reactive Protein (hs-CRP) (e.g., by at least 5%, 10%, 15%, 20%, 25%, 30%, 35%, 40%, 45% 50%, 55%, 60%, 65%, 70%, 75%, 80%, 85%, 90%, 95%, or 100%.) relative to the plasma concentration of D-Dimer or Highly Sensitive C Reactive Protein (hs-CRP) prior to administration of the respective MK-7 and/or MKH2-7.

In certain embodiments, prior to administration of the composition, the subject has a uremic oxidative blockade. In certain embodiments, the presence of a uremic oxidative blockade is determined by measuring increased plasma lipid peroxidation, e.g., by detection of increased F2 isoprostanes (Morrow et al. (1990) "A series of prostaglandin F2-like compounds are produced in vivo by humans by a non-cyclooxygenase, free radical-catalyzed mechanism," PROC. NATL. ACAD. SCI. USA 87:9383-9387), increased isolevuglandin-plasma protein adducts (Salomon et al. (2000) "Isolevuglandin-protein adducts in humans: Products of free radical-induced lipid oxidation through the isoprostane pathway," BIOCHIM BIOPHYS ACTA 1485:225-235), increased breath ethane (Handelman et al. (2000) J AM. SOC. NEPHROL. 11:271A); increased protein and amino acid oxidation, e.g., by detection of tyrosine residue oxidation (Heinecke et al. (1999) "Detecting oxidative modification of biomolecules with isotope dilution mass spectrometry: Sensitive and quantitative assays for oxidized amino acids in proteins and tissues," METHODS ENZYMOL. 300:124-144), cysteine or methionine residue oxidation, lysine oxidation and threonine oxidation, thiol oxidation and carbonyl formation in plasma proteins (Himmelfarb et al. (2000) "Plasma protein thiol oxidation and carbonyl formation in chronic renal failure," KIDNEY INT. 58:2571-2578); reactive aldehyde formation, e.g., by detecting glyoxal, methylglyoxal, acrolein, glycoaldehyde, and parahydroxy phenacetaldehyde (Miyata et al. (1999) "Alterations in nonenzymatic biochemistry in uremia: Origin and significance of 'carbonyl stress' in long-term uremic complications. KIDNEY INT. 55:389-399); increased reactive carbonyl compounds, e.g., by measuring hydrazine formation after reaction with 2,4-dinitrophenylhydrazine; diminished plasma glutathione levels and glutathione peroxidase function (Ceballos-Picot et al. (1996) "Glutathione antioxidant system as a marker of oxidative stress in chronic renal failure," FREE RADIC. BIOL. MED. 21:845-853); and increased ratio of oxidized to reduced thiols (Hultberg et al. (1995) "Reduced, free, and, total fractions of homocysteine and other thiol compounds in plasma from patients with renal failure," NEPHRON 70:62-67; Himmelfarb et al. (2002) "Plasma aminothiol oxidation in chronic renal failure," KIDNEY INT 61:705-716; Ward et al. "Polymorphonuclear leukocyte oxidative burst is enhanced in patients with chronic renal insufficiency," J AM. SOC. NEPHROL. 5:1697-1702).

In certain embodiments, the subject is receiving a statin. For example, the statin can be selected from simvastatin, lovastatin, atorvastatin, pravastatin, pitavastatin, rosuvastatin, and fluvastatin.

In certain embodiments of any of the above aspects, the method can include administering from about 2 mg to about 1,000 mg of MK-7 and/or MKH2-7 to the subject per day. In other embodiments, the method can include administering from about 5 mg to about 1,000 mg of MK-7 and/or MKH2-7 to the subject per day.

In certain embodiments of any of the above aspects, the method can include administering from about 2 mg to about 750 mg of MK-7 and/or MKH2-7 to the subject per day. In other embodiments, the method can include administering from about 5 mg to about 750 mg of MK-7 and/or MKH2-7 to the subject per day. In certain embodiments of any of the above aspects, the method can include administering from about 2 mg to about 500 mg of MK-7 and/or MKH2-7 to the subject per day. In other embodiments, the method can include administering from about 5 mg to about 500 mg of MK-7 and/or MKH2-7 to the subject per day. In certain embodiments of any of the above aspects, the method can include administering from about 2 mg to about 250 mg of MK-7 and/or MKH2-7 to the subject per day. In other embodiments, the method can include administering from about 5 mg to about 250 mg of MK-7 and/or MKH2-7 to the subject per day. In certain embodiments of any of the above aspects, the method can include administering from about 2 mg to about 100 mg of MK-7 and/or MKH2-7 to the subject per day. In other embodiments, the method can include administering from about 5 mg to about 100 mg of MK-7 and/or MKH2-7 to the subject per day. In other embodiments, the method can include administering from about 10 mg to about 75 mg of MK-7 and/or MKH2-7 to the subject per day, e.g., administering 10, 25, 50 or 75 mg of MK-7 and/or MKH2-7 to the subject per day.

In certain embodiments, the MK-7 and/or MKH2-7 is administered to the subject for at least 2 weeks, 4 weeks, 6 weeks, 8 weeks, 3 months, 6 months, 1 year, or indefinitely. If the subject is undergoing hemodialysis, the MK-7 and/or MKH2-7 can be administered to the subject for a period that includes at least the duration of hemodialysis.

In certain embodiments, the MK-7 and/or MKH2-7 is administered orally. The MK-7 and/or MKH2-7 can be disposed within a tablet, caplet or capsule. The MK-7 and/or MKH2-7 can be present in a composition comprising a pharmaceutically acceptable excipient.

The description above describes multiple aspects and embodiments of the invention. The patent application specifically contemplates all combinations and permutations of the aspects and embodiments. These and other aspects and features of the invention are described in the following detailed description and claims.

BRIEF DESCRIPTION OF THE DRAWINGS

The foregoing and other objects, features and advantages of the invention will become apparent from the following description of preferred embodiments, as illustrated in the accompanying drawings. Like referenced elements identify common features in the corresponding drawings, in which.

DETAILED DESCRIPTION

Figure 1:
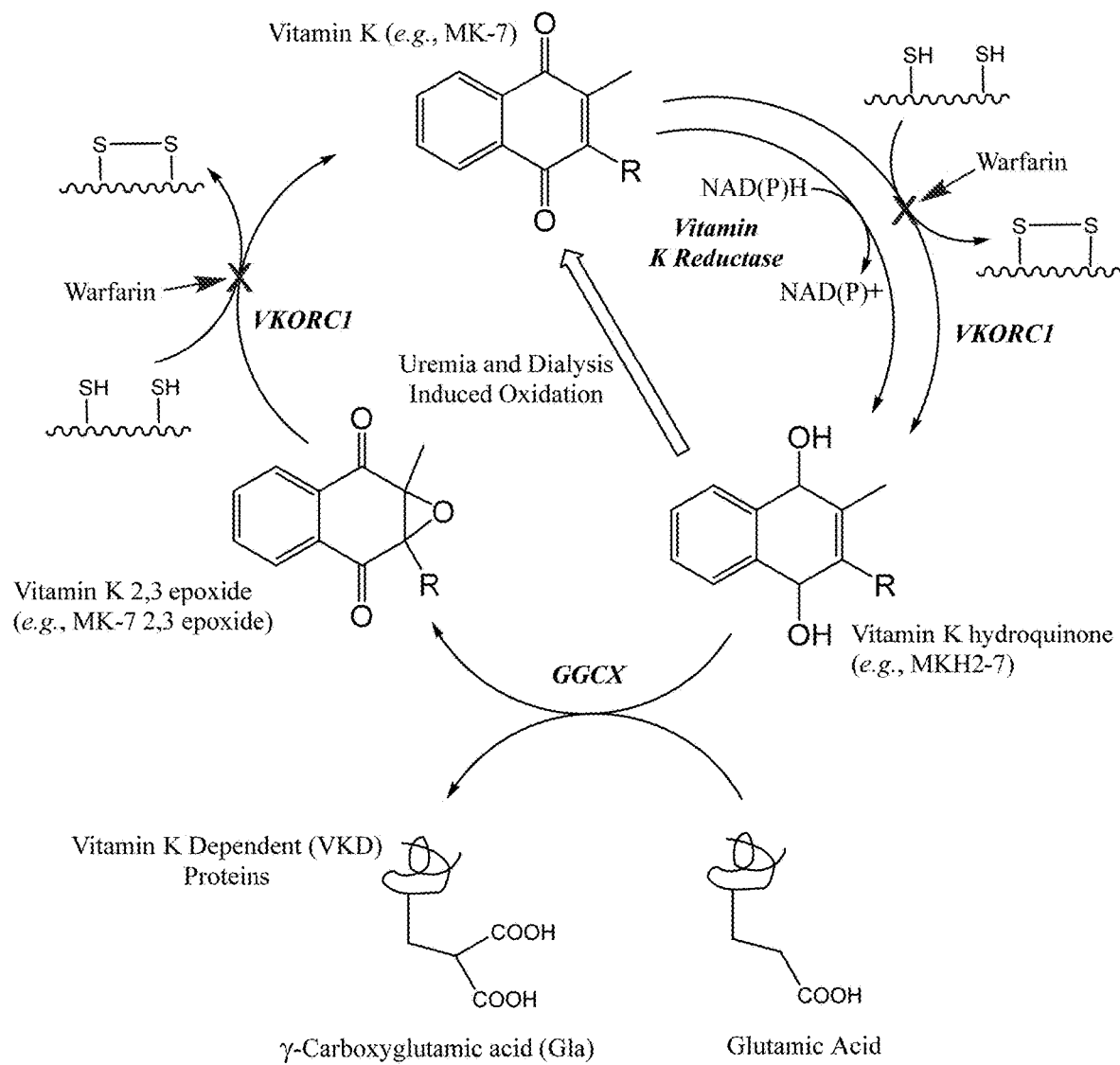
FIG. 1 is a schematic diagram depicting the Vitamin K cycle and the effects of uremia and hemodialysis-induced oxidation of Vitamin K hydroquinone.
Figure 1:
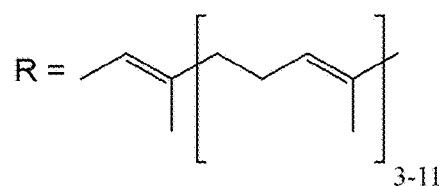
Figure 2:
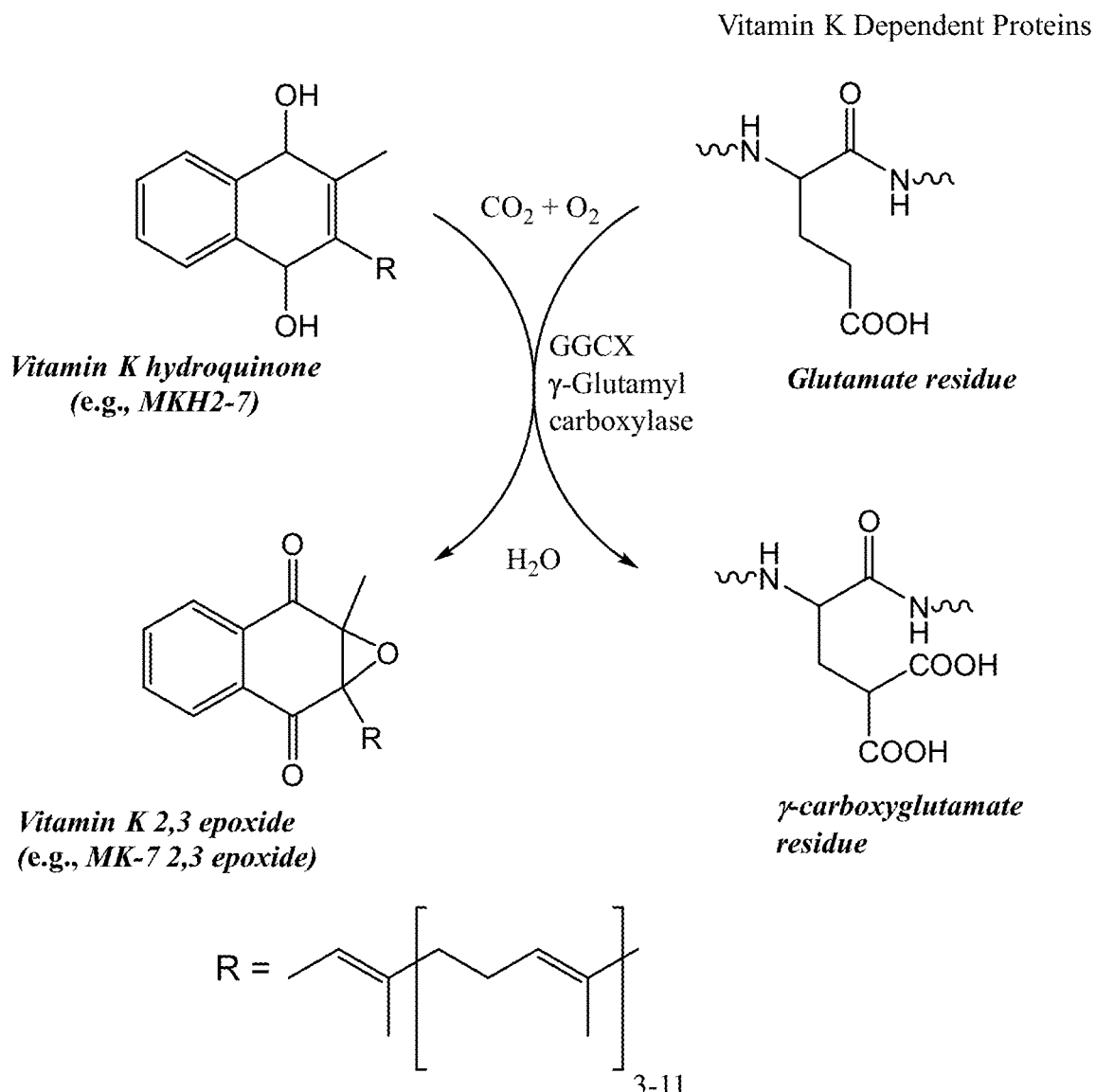
FIG. 2 is a schematic diagram depicting the carboxylation of Vitamin K-dependent proteins by gamma-glutamate carboxylase (GGCX).

The invention is based, in part, upon the discovery that menaquinone-7 (MK-7) and/or menaquinol-7 (MKH2-7), the reduced form of MK-7, can be administered to a subject in need thereof to prevent or treat (e.g., slow the progression of, arrest, and/or reverse) calciphylaxis in the subject, e.g., a subject with diabetes and/or chronic kidney disease.

Without wishing to be bound by the theory, it is believed that oxidative stress induced by the retention of uremic toxins depletes vascular endothelium of functional Vitamin $K_2$ leading to suboptimal concentrations of certain Vitamin K-dependent proteins, including carboxylated MGP and activated Protein C. The subsequent reduced calcium binding capacity of these and other vitamin-dependent proteins contributes to abnormal tissue calcification. High doses of substantially pure MK-7 and/or MKH2-7 can be used to increase carboxylation of Vitamin K-dependent proteins, thereby preventing or treating (e.g., slowing the progression of, arresting, and/or reversing) calciphylaxis, wherein the MK-7 and/or MKH2-7 are administered in the form of a pharmaceutical composition. The MK-7 and/or MKH2-7 can be administered in a single dosage unit (for example, a single capsule) or in multiple dosage units (for example, multiple capsules) provided that the requisite amount of MK-7 and/or MKH2-7 is administered per day. In certain embodiments, the pharmaceutical composition comprises MK-7. In certain embodiments, the pharmaceutical composition comprises MKH2-7. In certain embodiments, the pharmaceutical composition comprises a combination of MK-7 and MKH2-7.

I. Menaquinone-7 (MK-7) and/or Menaquinol (MKH2-7)

The compositions of the invention comprise menaquinone-7 (MK-7), a form of Vitamin $K_2$. The IUPAC name for MK-7 is as 2-[(2E,6E,10E,14E,18E,22E)-3,7,11,15,19,23,27-heptamethyloctacosa-2,6,10,14,18,22,26-heptaenyl]-3-methylnaphthalene-1,4-dione, and the chemical structure of NIK-7 is shown in Formula I.

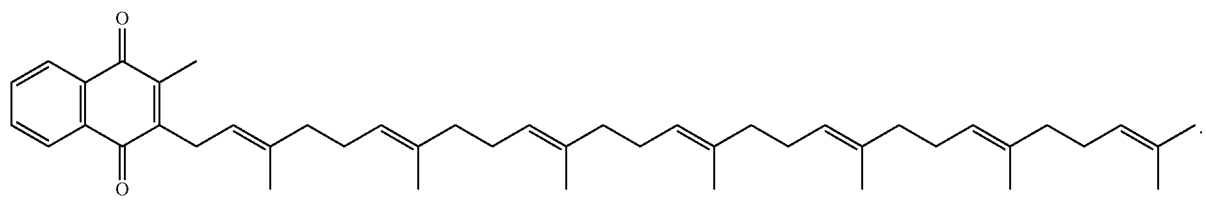

(Formula I)

Also contemplated for use in accordance with the methods herein is menaquinol-7 (MKH2-7), which is a reduced form of MK-7. The IUPAC name for MKH2-7 is 2-[(2E, 6E,10E,14E,18E,22E)-3,7,11,15,19,23,27-heptamethyloctacosa-2,6,10,14,18,22,26-heptaenyl]-3-methylnaphthalene-1,4-diol, and the chemical structure of MKH2-7 is set forth in Formula II:

(Formula II)

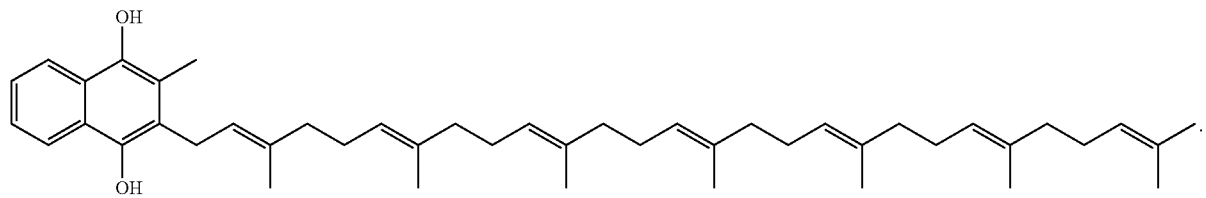

Without wishing to be bound by the theory, it is believed that supplemental MK-7 and/or MKH2-7 forms of Vitamin K provide increased protection against non-specific oxidation of Vitamin K intermediates caused by uremia and/or dialysis.

The long aliphatic chain of MK-7 is not synthesized by humans but is synthesized in the colon by bacteria. Also, dietary sources of MK-7 include bacterially fermented foods such as nattō (soy beans fermented by *Bacillus subtilis*), cheeses, sauerkraut and buttermilk and pork, eel, plaice, and buckwheat bread. In addition, MK-7 is available as a nutritional supplement (e.g., Vitamin K2 MK-7 from Rejuvenation Therapeutics®; Bio-Tech™ Pharmacal MK-7 Vitamin K2, Fayetteville Ark.; NOW® Foods MK-7 Vitamin K-2).

The invention, however, employs substantially pure MK-7 and/or MKH2-7, administered in the form of a pharmaceutical composition.

MK-7 can also be produced synthetically, for example, as described in Baj et al. (2016) "Convergent Synthesis of Menaquinone-7 (MK-7)," ORG. PROCESS RES. DEV. 20:1026-1033, WO2010/034999 and WO2010/035000 (also published as U.S. Patent Application No. 2011/0207967).

MKH2-7 can be synthesized from MK-7 by reducing MK-7 using conventional reduction reactions known in the art, including, for example, by reduction with zinc and acetic acid as described by Marchand et al. (1991) "Mild and Highly Selective Ultrasound-promoted Zinc/Acetic Acid Reduction of C=C Bonds in α,β-Unsaturated γ-Dicarbonyl Compounds," SYNTHESIS 1991(3):198-200.

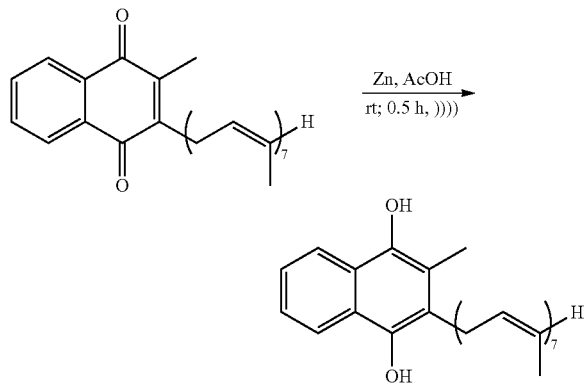

In this method, MK-7 (e.g., 1 g, 1.54 mmol) is dissolved in acetic acid glacial (15 mL) and powdered zinc (e.g., 0.8 g, 12.3 mmol) is added. The resulting mixture is sonicated for 0.5 hour or the reaction can be refluxed until completion. The resulting mixture is filtered and the residue is washed with dichloromethane. The combined filtrates are concentrated in vacuo, to produce the pure reduction product. The procedure is performed under Argon. To stabilize MKH2-7 in the reduced form it may be helpful to admix MKH2-7 with one or more antioxidants such as vitamin C, a vitamin C ester (e.g., ascorbyl palmitate), and/or vitamin E, e.g., within a capsule or softgel. Alternatively, prodrugs of MKH2-7 can be created, for example, where one or both of the hydroxyl groups are esterified with various groups (for example, acetate) to produce a stable prodrug that is metabolized to produce MKH2-7 in the subject.

II. Dosage Forms and Administration

In certain embodiments, compositions useful in accordance with the invention comprise, consist essentially of, or consist of substantially pure MK-7 and/or MKH2-7. Substantially pure refers to a composition of active ingredient comprising at least 95%, at least 96%, at least 97%, at least 98%, at least 99% or at least 99.5% by weight MK-7 and/or MKH2-7. In certain embodiments, MK-7 and/or MKH2-7 are the sole vitamins administered in a dosage form.

As used herein, the phrases "effective amount" and "therapeutically effective amount" refer to the amount of a compound (e.g., MK-7 and/or MKH2-7) sufficient to effect one or more beneficial or desired results. An effective amount can be administered in one or more administrations, applications or dosages and is not intended to be limited to a particular formulation or administration route.

In another embodiment, the invention provides a dosage form, for example, an oral dosage form, comprising an effective amount of MK-7 and/or MKH2-7, for example, from about 2 mg to about 1,000 mg, from about 2 mg to about 750 mg, from about 2 mg to about 500 mg, from about 2 mg to about 250 mg, from about 2 mg to about 200 mg, from about 2 mg to about 150 mg, from about 2 mg to about 100 mg, from about 2 mg to about 50 mg, from about 2 mg to about 25 mg, from about 5 mg to about 1,000 mg, from about 5 mg to about 750 mg, from about 5 mg to about 500 mg, from about 5 mg to about 250 mg, from about 5 mg to about 200 mg, from about 5 mg to about 150 mg, from about 5 mg to about 100 mg, from about 5 mg to about 50 mg, from about 5 mg to about 25 mg, from about 10 mg to about 1,000 mg, from about 10 mg to about 750 mg, from about 10 mg to about 500 mg, from about 10 mg to about 250 mg, from about 10 mg to about 200 mg, from about 10 mg to about 150 mg, from about 10 mg to about 100 mg, from about 10 mg to about 50 mg, from about 10 mg to about 25 mg, from about 15 mg to about 1,000 mg, from about 15 mg to about 750 mg, from about 15 mg to about 500 mg, from about 15 mg to about 250 mg, from about 15 mg to about 200 mg, from about 15 mg to about 150 mg, from about 15 mg to about 100 mg, from about 15 mg to about 50 mg, from about 15 mg to about 25 mg, from about 25 mg to about 1,000 mg, from about 25 mg to about 750 mg, from about 25 mg to about 500 mg, from about 25 mg to about 250 mg, from about 25 mg to about 200 mg, from about 25 mg to about 150 mg, from about 25 mg to about 100 mg, from about 25 mg to about 50 mg, from about 50 mg to about 1,000 mg, from about 50 mg to about 750 mg, from about 10 mg to about 500 mg, from about 50 mg to about 250 mg, from about 50 mg to about 200 mg, from about 50 mg to about 150 mg, from about 50 mg to about 100 mg, from about 75 mg to about 1,000 mg, from about 75 mg to about 750 mg, from about 75 mg to about 500 mg, from about 75 mg to about 250 mg, from about 75 mg to about 200 mg, from about 75 mg to about 150 mg, from about 75 mg to about 100 mg, from about 100 mg to about 1,000 mg, from about 100 mg to about 750 mg, from about 100 mg to about 500 mg, from about 100 mg to about 250 mg, from about 100 mg to about 200 mg, or from about 100 mg to about 150 mg. In certain embodiments, 2 mg, 5 mg, 10 mg, 25 mg, 75 mg or 100 mg of substantially pure MK-7 and/or MKH2-7 is administered to the subject in a suitable dosage form, such as a tablet, caplet or capsule (e.g., a liquid or gel capsule).

In certain embodiments, the methods can include administering from about 2 mg to about 100 mg of MK-7 and/or MKH2-7 to the subject per day. In other embodiments, the method can include administering from about 2.5 mg to about 100 mg, from about 3 mg to about 100 mg, from about 4 mg to about 100 mg, or from about 5 mg to about 100 mg of MK-7 and/or MKH2-7 to the subject per day. In certain embodiments, the method can include administering about 2 mg, 2.5 mg, about 3 mg, about 4 mg, about 5 mg, about or 7.5 mg of MK-7 and/or MKH2-7 to the subject per day. In other embodiments, the method can include administering from about 10 mg to about 100 mg of MK-7 and/or MKH2-7 to the subject per day, e.g., administering 10, 25, 50, 75 or 100 mg of MK-7 and/or MKH2-7 to the subject per day.

It is understood that the MK-7 and/or MKH2-7 can be administered in a single dosage unit (e.g., 1 capsule) or in multiple (e.g., 2, 3, or 4, etc.) dosage units (e.g., multiple capsules). A composition for use in accordance with the invention can be formulated as one or more dosage units. Such dosage units may be administered once a day or a plurality (e.g., 1 to about 10, 1 to about 8, 1 to about 6, 1 to about 4 or 1 to 2) of times per day, or as many times as needed to elicit a therapeutic response. The dosage units can be packaged in a kit, for example, a kit containing one or more blister packages of about 1 to about 20 dosage units (e.g., capsules) per sheet or a bottle containing a plurality of dosage units (e.g., capsules).

In certain embodiments, the pharmaceutical composition containing the MK-7 and/or MKH2-7 can be formulated for administration in solid or liquid form, including drenches (aqueous or non-aqueous solutions or suspensions), tablets (e.g., those targeted for buccal, sublingual, and/or systemic absorption), boluses, powders, granules, pastes for application to the tongue, and/or topical creams. As used herein, the term "pharmaceutical composition" refers to the combination of an active agent with one or more pharmaceutically acceptable carriers (inert or active) making the composition especially suitable for diagnostic or therapeutic use in vivo or ex vivo. As used herein, the term "pharmaceutically acceptable carrier" refers to any of the standard pharmaceutical carriers and excipients, such as a phosphate buffered saline solution, water, emulsions (e.g., such as an oil/water or water/oil emulsions), and various types of wetting agents.

The compositions also can include stabilizers and preservatives. For examples of carriers, stabilizers and adjuvants, see Martin, Remington's Pharmaceutical Sciences, 15th Ed., Mack Publ. Co., Easton, Pa. (1975).

In certain embodiments, the MK-7 and/or MKH2-7 composition can be formulated in an oil, such as castor oil, sesame oil, medium chain triglyceride (MCT) oil, olive oil, soybean oil, or coffee bean oil. Excipients suitable for use with the MK-7 and/or MKH2-7 composition include antioxidants, bioavailability enhancers, solubility enhancers or solubilizers, stabilizers, etc.

In certain embodiments, the MK-7 and/or MKH2-7 composition includes one or more antioxidants such as one or more antioxidants selected from DL-alpha tocopherol (vitamin E), ascorbic acid (vitamin C) or a vitamin C ester, docosahexaenoic acid (DHA), eicosapentaenoic acid (EPA), lecithin, citric acid, sesame oil, olive oil, soybean oil, and coffee bean oil.

In certain embodiments, the MK-7 and/or MKH2-7 composition includes an emulsifier selected from Tween® 20 (polyethylene glycol sorbitan monolaurate), Tween® 80 (polyethylene glycol sorbitan monooleate), Kolliphor® EL (polyoxyl castor oil, also called Cremophor EL), Capmul® MCM (mono-diglyceride of medium chain fatty acids such as caprylic and capric), lecithin, Lauroglycol™ 90 (propylene glycol monolaurate (type II)), deoxycholic acid, Phosal® 50 PG (lecithin in propylene glycol, sunflower mono-diglycerides, ascorbyl palmitate), beeswax, and wax flakes.

In certain embodiments, the MK-7 and/or MKH2-7 composition includes a bioavailability enhancer selected from Maisine® CC (glyceryl monolinoleate), Gelucire® 44/14 (lauroyl polyoxyl-32 glycerides), Capmul® PG-8 NF (propylene glycol monoester of caprylic acid), Plurol® Oleique (polyglyceryl-6 dioleate), Lauroglycol™ 90 (propylene glycol monolaurate (type II), Labrasol® (caprylocaproyl polyoxyl-8 glycerides), Captisol® (SBE-beta-cyclodextrin), Labrafil® M2125CS (linoleoyl Polyoxyl-6 glycerides), and Phosal® 50 PG (lecithin in propylene glycol, sunflower mono-diglycerides, ascorbyl palmitate).

In certain embodiments, the MK-7 and/or MKH2-7 composition includes a solubility enhancer or solubilizer selected from oleic acid, Kolliphor® EL (polyoxyl castor oil, also called Cremophor EL), Vitamin E TPGS (D-α-tocopherol polyethylene glycol-1000 succinate), Maisine® CC (glyceryl monolinoleate), Gelucire® 44/14 (lauroyl polyoxyl-32 glycerides), Miglyol® 812N (esters of saturated coconut and palm kernel oil-derived caprylic fatty acids and glycerin), Plurol® Oleique (Polyglyceryl-6 Dioleate), Lauroglycol™ 90 (propylene glycol monolaurate (type II), Labrasol® (Caprylocaproyl polyoxyl-8 glycerides), Kolliphor® EL (polyoxyl castor oil), Captisol® (SBE-beta-cyclodextrin), Encapsin™ HPB (hydroxypropyl-beta-cyclodextrin), Peceol™ (glycerol/glyceryl monooleate (type 40)), sodium deoxycholate, deoxycholic acid, Labrafil® M2125CS (linoleoyl Polyoxyl-6 glycerides), and medium-chain mono- and diglycerides.

In certain embodiments, the MK-7 and/or MKH2-7 composition includes a solvent selected from the group consisting of isopropyl myristate, Capmul® PG-8 NF (propylene glycol monoester of caprylic acid), Lauroglycol™ 90 (propylene glycol monolaurate (type II)), Polyethylene glycol (PEG), and propylene glycol.

In certain embodiments, the MK-7 and/or MKH2-7 composition includes a stabilizer selected from the group consisting of oleic acid and DL-alpha tocopherol.

In certain embodiments, the MK-7 and/or MKH2-7 composition includes a surfactant selected from the group consisting of sodium oleate, Span 20 (sorbitan laurate), Span® 80 (sorbitan oleate), Vitamin E TPGS (D-α-tocopherol polyethylene glycol-1000 succinate), Lauroglycol™ 90 (propylene glycol monolaurate (type II)), Labrasol® (Caprylocaproyl polyoxyl-8 glycerides), polyethylene glycol (PEG), and Captisol® (SBE-beta-cyclodextrin).

Other suitable excipients include one or more fatty acids selected from lauric, valeric, caproic, capric, caprylic, myristic, palmitic, palmitoleic, stearic, and arachidic acid and their esters.

In certain embodiments, compositions useful in the practice of the invention are orally deliverable. The terms "orally deliverable" or "oral administration" herein include any form of delivery of the compositions described herein to a subject, wherein the composition is placed in the mouth of the subject, whether or not the composition is swallowed. Thus "oral administration" includes buccal and sublingual as well as esophageal administration.

In certain embodiments, the MK-7 and/or MKH2-7 is administered to the subject for at least 2 weeks, e.g., 2, 3, 4, 5 weeks, or more. In certain embodiments, the MK-7 and/or MKH2-7 is administered for at least 6 weeks. In certain embodiments, the MK-7 and/or MKH2-7 is administered to a subject for at least 2 months, at least 3 months, at least 6 months, at least 1 year, at least 2 years, at least 3 years, or indefinitely. In certain embodiments, the MK-7 and/or MKH2-7 is administered at least as long as the subject is receiving an anticoagulant therapy that is not warfarin or a drug having a similar mechanism of action as warfarin (e.g., acenocoumarol and phenprocoumon) and/or statin therapy. If the subject is undergoing hemodialysis, the MK-7 and/or MKH2-7 can be administered to the subject for a period that includes the duration of hemodialysis.

In certain embodiments, the MK-7 and/or MKH2-7 composition is administered together with a statin such as simvastatin, lovastatin, atorvastatin, pravastatin, pitavastatin, rosuvastatin, and fluvastatin. The MK-7 and/or MKH2-7 composition can be formulated into a single dosage form, such as a dosage form discussed herein, with the statin. In other embodiments, the MK-7 and/or MKH2-7 composition is formulated into a separate dosage form from the statin. Formulation of statins, such as simvastatin, lovastatin, atorvastatin, pravastatin, pitavastatin, rosuvastatin, and fluvastatin, is well known in the art.

As used herein, the terms "subject" and "patient" are used interchangeably and refer to an organism to be treated by the methods and compositions of the present invention. Such organisms are preferably mammals (e.g., human, mouse, rat, guinea pig, dog, cat, horse, cow, pig, or non-human primate, such as a monkey, chimpanzee, baboon, and rhesus), and more preferably humans.

III. Methods

In certain aspects, the invention provides a method of preventing or treating (e.g., slowing the progression of, arresting, and/or reversing) calciphylaxis in a subject in need thereof. In certain embodiments, the method relates to preventing or slowing the progression of calciphylaxis. In certain embodiments, the method relates to arresting the progression of calciphylaxis. In certain embodiments, the method relates to reversing calciphylaxis.

The method can include administering to the subject a menaquinone-7 (MK-7) and/or menaquinol-7 (MKH2-7) composition as described herein (e.g., at least 2 mg of substantially pure MK-7 and/or MKH2-7 per day, e.g., 10, 15, 25, 50 or 75 mg per day), thereby to prevent, slow the progression of, or reverse calciphylaxis. In certain embodiments, the subject has distal calciphylaxis (i.e., affecting the limbs) and/or central calciphylaxis (i.e., affecting the thorax).

In certain aspects, the invention provides a method of improving aortic compliance in a subject with calciphylaxis, the method comprising administering to the subject an effective amount of substantially pure menaquinone-7 (MK-7) and/or menaquinol-7 (MKH2-7) per day. In certain embodiments, the invention provides a method of preventing or treating (e.g., slowing the progression of, arresting, and/or reversing) peripheral vasculopathy in a subject in need thereof, wherein the subject has ESRD or CKD, the method comprising administering to the subject an effective amount of substantially pure menaquinone-7 (MK-7) and/or menaquinol-7 (MKH2-7) per day.

As used herein, the term "treating" includes any effect, for example, lessening, reducing, modulating, arresting, slowing the progression of, ameliorating or eliminating, that results in the improvement of the condition, disease, disorder, and the like, or ameliorating a symptom thereof. Treating can be curing, improving, or at least partially ameliorating the disorder. In certain embodiments, treating is curing the disease. The term "disorder" refers to and is used interchangeably with, the terms disease, condition, or illness, unless otherwise indicated.

1. Diabetes, CKD, ESRD, Hemodialysis

In certain embodiments, the subject to be treated with the methods and/or compositions described herein has been diagnosed as pre-diabetic or has diabetes, e.g., type I or II diabetes. Diabetes often leads to chronic kidney disease (CKD) due to uncontrolled blood sugar and blood pressure damaging capillaries in the kidney. CKD often leads to the development of uremia (urea in the blood), which can inhibit cyclic regeneration of Vitamin K, leading to calciphylaxis. Accordingly, in certain embodiments, the subject has CKD.

Patients with chronic kidney disease are classified into stages based upon their glomerular filtration rate (GFR). The GFR for stage 1 patients is >90 mL/minute/1.73 m$^2$, stage 2 is 60-89 mL/minute/1.73 m$^2$, stage 3 is 30-59 mL/minute/ 1.73 m$^2$, stage 4 is 15-29 mL/minute/1.73 m$^2$, and stage 5 is <15 mL/minute/1.73 m$^2$. In certain embodiments, the subject has stage 3, stage 4, or stage 5 CKD. Patients with stage 4 or 5 CKD are considered to have end stage renal disease (ESRD). Other types of kidney disease, such as polycystic kidney disease, also can lead to ESRD. In certain embodiments, the subject has ESRD.

Patients with CKD and/or ESRD often require hemodialysis. However, hemodialysis can lead to the oxidation of numerous tissue proteins, and both CKD and ESRD patients often exhibit a higher percentage (15-fold) of carbonyl proteins compared to normal controls. The percentage of carbonyl proteins may be even higher among patients receiving hemodialysis, suggesting that hemodialysis contributes to oxidative burden.

As discussed supra, the oxidative load generated by hemodialysis is believed to lead to the oxidation of MKH2-7 back to MK-7. It is contemplated that the oxidation of Vitamin K hydroquinone (KH2) by hemodialysis blocks its ability to function as a co-factor for GGCX leading to reduced gamma carboxylation of Vitamin K-dependent proteins. Thus, the oxidative effects of hemodialysis may contribute to the calciphylaxis observed within the CKD and ESRD populations. Accordingly, in certain embodiments herein, the subject is receiving hemodialysis.

2. Anticoagulant Therapy

Vitamin K is necessary for the production of clotting factors. However, certain anticoagulants, for example, certain oral anticoagulants, act as Vitamin K antagonists to prevent blood clotting. Given that calciphylaxis can occur when Vitamin K activity is dysregulated, the methods herein relate to preventing or treating (e.g., slowing the progression of, arresting, and/or reversing) calciphylaxis in a subject receiving anticoagulant therapy, and in need thereof, comprising administering to the subject a menaquinone-7 (MK-7) and/or menaquinol-7 (MKH2-7) containing composition as described herein, thereby to prevent or treat calciphylaxis.

Exemplary anti-coagulant therapies include inhibitors of Factor Xa activity or Factor IIa activity. Inhibitors of Factor Xa activity include the oral therapies apixaban (e.g., Eliquis®, Bristol-Myers Squibb), rivaroxaban (e.g., Xarelto®, Janssen), betrixaban (e.g., Bevyxxa®, Portola Pharmaceuticals), and edoxaban (e.g., Savaysa®, Daiichi Sankyo), and the subcutaneous therapy fondaparinux (e.g., Arixtra®, GlaxoSmithKline). Inhibitors of Factor IIa (thrombin) activity include the oral therapies dabigratran (e.g., Pradaxa®, Boehringer Ingelheim) and the intravenous therapy argatroban (e.g., Pfizer).

In certain embodiments, the subject is simultaneously receiving a non-warfarin-based anticoagulant therapy. Non-warfarin-based anticoagulant therapies can be based on an anticoagulant that does not primarily act to block the conversion of Vitamin K to Vitamin K hydroquinone and/or the conversion of Vitamin K 2,3-epoxide back to Vitamin K. Exemplary non-warfarin-based anticoagulants may act as a inhibitor of Factor Xa activity or an inhibitor of Factor IIa activity. Exemplary non-warfarin-based anticoagulants include apixaban, rivaroxaban, betrixaban, edoxaban, dabigratran, fondaparinux, and argatroban. In certain embodiments, the subject has previously been exposed to warfarin-based anti-coagulation therapy.

In certain embodiments, the methods described herein relate to preventing, slowing the progression of, arresting, and/or reversing calciphylaxis in a subject in need thereof, wherein the subject has stage 5 CKD and is undergoing oral, non-warfarin-based anticoagulant therapy. The method can comprise administering to the subject at least 2 mg of substantially pure menaquinone-7 (MK-7) and/or menaquinol-7 (MKH2-7) per day, thereby to prevent or treat (e.g., slow the progression of, arrest, and/or reverse) calciphylaxis. The subject may also have diabetes and/or may be undergoing hemodialysis.

3. Statin Therapy

It has been observed that coronary artery calcification can be increased upon statin use (Saremi et al. (2012) "Progression of Vascular Calcification Is Increased With Statin Use in the Veterans Affairs Diabetes Trial (VADT)," DIABETES CARE 35:2390-2392). Lipophilic statins have been shown to inhibit the enzymatic activity of UbiA prenyltransfease domain-containing protein (UBIAD1), an enzyme that plays a role in Vitamin K synthesis (Nakagawa et al. (2010) "Identification of UBIAD1 as a novel human menaquinone-4 biosynthetic enzyme," NATURE 468(7320):117-21). Further, in vitro experiments appear to demonstrate that Vitamin K synthesis is impaired in the presence of statins (Chen et al. (2017) "Does statins promote vascular calcification in chronic kidney disease?" EUR. J. CLIN. INVEST. 47(2): 137-148).

Without wishing to be bound by the theory, it is contemplated that HMG coA reductase inhibitors directly inhibit MK-4 production in coronary vascular smooth muscle, which may explain why statins have not been shown to reduce cardiovascular mortality in CKD or ESRD patients. One possible explanation for this observation is that CDK and ESRD patients are functionally Vitamin K deficient, and that blocking endogenous vascular smooth muscle cell vitamin K (MK-4) production only serves to worsen the calcification of the media of the vessel, thus mitigating any potential benefits of lipid reduction. Moreover, the loss of vascular compliance accompanying the increase in calcification may contribute to overall cardiovascular mortality.

Accordingly, provided herein is a method for preventing or treating (e.g., slowing the progression of, arresting, and/or reversing) calciphylaxis in a subject in need thereof, wherein the subject is receiving a statin. The method can include administering to the subject a menaquinone-7 (MK-7) and/or menaquinol-7 (MKH2-7) composition as described herein. In certain embodiments, the subject is receiving a statin, such as simvastatin (e.g., Zocor®, Merck & Co., Inc.), lovastatin (e.g., Mevacor®, Merck & Co., Inc.), atorvastatin (e.g., Lipitor®, Pfizer), pravastatin (e.g., Pravachol®, Bristol-Myers Squibb Co.), pitavastatin (e.g., Livalo®, Kowa Pharmaceuticals America), rosuvastatin (e.g., Crestor®, AstraZeneca), and fluvastatin (e.g., Lescol®, Novartis Pharmaceuticals).

Further provided herein is a method for preventing or treating (e.g., slowing the progression of, arresting, and/or reversing) calciphylaxis in a subject in need thereof, wherein the method includes administering to the subject menaquinone-7 (MK-7) and/or menaquinol-7 (MKH2-7) composition as described herein and a statin, such as simvastatin, lovastatin, atorvastatin, pravastatin, pitavastatin, rosuvastatin, and fluvastatin. The menaquinone-7 (MK-7) and/or menaquinol-7 (MKH2-7) and statin can be administered as separate dosage forms, or in the same dosage form.

4. Improving Aortic Compliance, and Arresting and/or Reversing Peripheral Vasculopathy In certain embodiments, the disclosure relates to a method of arresting and/or reversing peripheral vasculopathy in a subject in need thereof, wherein the subject has ESRD or CKD, the method comprising administering to the subject an effective amount of substantially pure menaquinone-7 (MK-7) and/or menaquinol-7 (MKH2-7). In certain embodiments, the disclosure relates to a method of improving aortic compliance in a subject in need thereof, the method comprising administering to the subject an effective amount of substantially pure menaquinone-7 (MK-7) and/or menaquinol-7 (MKH2-7).

The term "vasculopathy" refers to any disease or disorder affecting blood vessels. It can include any inflammatory, metabolic, coagulative, embolic or degenerative disease, disorder, or condition. In certain embodiments, the vasculopathy is vascular calcification, e.g., medial or intimal vascular calcification.

One of the clinical consequences of vascular calcification is arterial stiffness, which leads to a decrease in vascular compliance (e.g., vascular elasticity), e.g., in aortic compliance. Thus, in accordance with the methods disclosed herein, administration of an effective amount of substantially pure menaquinone-7 (MK-7) and/or menaquinol-7 (MKH2-7) may improve aortic compliance. Reduction in aortic compliance can be assessed using aortic plethysmography (i.e., the capacity of a blood vessel to dilate), see, e.g., Inuma et al. (2012) HONG KONG JOURNAL OF NEPHROLOGY 14(2): 48-53. Reduction in aortic compliance also can be assessed by measuring pulse wave velocity (PWV). PWV is the velocity at which the arterial pulse moves through the circulatory system and is used as a measure of arterial stiffness. Higher PWV corresponds to higher arterial stiffness, and therefore lower vascular compliance. Methods for measuring PWV are known in the art and described, for example, by Pereira et al. (2015) "Novel Methods for Pulse Wave Velocity Measurement," J. MED. BIOL. ENG. 35:555-565. Briefly, PWV can be assessed by measuring regional PWV, such as carotid-femoral PWV, or local PWV. Methods for measuring regional PWV are known in the art and include, for example, the use of a pulse transducer probe, TY-360 pressure transducer, doppler unit synchronism with electrocardiogram (ECG), pulse transducer probes, photoplethysmography, Complior® (piezoelectric pressure transducers), SphygmoCor®, Arteriograph®, and PulsePen® (tonometer and integrated electrocardiogram unit). Id. Methods for measuring local PWV are known in the art and include, for example, magnetic resonance imaging, ultrasound, and angiography. Id.

In certain embodiments, administration of the MK-7 and/or MKH2-7 increases aortic compliance of a blood vessel by at least 5%, 10%, 15%, 20%, 25%, 30%, 35%, 40%, 45% 50%, 55%, 60%, 65%, 70%, 75%, 80%, 85%, 90%, 95%, or 100%. In certain embodiments, administration of the MK-7 and/or MKH2-7 increases aortic compliance of a blood vessel by about 10%-500%, by about 50%-200%, by about 75%-125%. In certain embodiments, administration of the MK-7 and/or MKH2-7 increases aortic compliance of a blood vessel by at least 5%, 10%, 15%, 20%, 25%, 30%, 35%, 40%, 45% 50%, 55%, 60%, 65%, 70%, 75%, 80%, 85%, 90%, 95%, or 100% relative to a vessel prior to administration of the MK-7 and/or MKH2-7. In certain embodiments, administration of the MK-7 and/or MKH2-7 increases aortic compliance of a blood vessel by about 10%-500%, by about 50%-200%, by about 75%-125% relative to a vessel prior to administration of the MK-7 and/or MKH2-7.

Coronary arterial calcium scores (CAC) can be used to estimate the extent of calcification of thoracic arteries. A high CAC score is indicative of calcification, and treatment has the aim of arresting the long term increase in CAC score, or reversing it, or slowing the rate of increase.

5. Chronic Obstructive Pulmonary Disease

Chronic Obstructive Pulmonary Disease is a term used to describe progressive lung disease that makes breathing difficult. The two primary forms of COPD are emphysema and chronic bronchitis. Symptoms of COPD include difficulty breathing, cough, mucus production, and wheezing. In addition, elastinolysis (proteolysis of elastin) is a key feature of COPD. It contributes to the loss of arterial flexibility and promotes calcification of the intimal media of blood vessels. It also has been shown to be a strong predictor of mortality in COPD patients (Rabinovich et al., (2016) "Circulating desmosine levels do not predict emphysema progression but are associated with cardiovascular risk and mortality in COPD," ERJ Express doi: 10.1183/13993003.01824-2015). MGP has been demonstrated to inhibit the production of matrix metalloproteases that promote elastinolysis. Therefore, it has been hypothesized that Vitamin D is a critical determinant of the rate of elastin degradation, and that low Vitamin D levels lead to low MGP activity that is inadequate to protect from elastinolysis (Piscaer et al., (2017) "Vitamin D deficiency: the linking pin between COPD and cardiovascular diseases?" RESP. RES. 18:189). Without wishing to be bound by the theory, enhanced production of activated (carboxylated) MGP by administration of MK-7 and/or MKH2-7 can act to suppress the deleterious effects of elastinolysis in a subject having COPD thereby to prevent, or slow the progression of, or reverse the one or more symptoms of COPD.

Reduction of symptoms of COPD, including difficulty breathing, cough, mucus production, and wheezing, can be measured by any means known in the art. A slowing of the rate of increase of one or more COPD symptoms over time is indicative of a slowing of the progression of the one or more symptoms of COPD, or a reduction in one or more symptoms, such as by 5%, 10%, 15%, 20%, 25%, 30%, 35%, 40%, 45% 50%, 55%, 60%, 65%, 70%, 75%, 80%, 85%, 90%, 95%, or 100% is indicative of a reversal of the one or more symptoms of COPD.

Elastinolysis can be measured by any method known in the art, including, for example, by measuring blood isodesmosine levels in a subject. A slowing of the rate of increase in isodesmosine levels over time is indicative of a slowing of the progression of the one or more symptoms of COPD, or a reduction in isodesmosine levels, such as by 5%, 10%, 20%, 25%, 30%, 35%, 40%, 50%, 60%, 70%, 80%, 90% or 100% is indicative of a reversal of the one or more symptoms of COPD.

6. Hyperparathyroidism

The incidence of calciphylaxis appears to be increasing, which may be due, in part, to the administration of calcium-based phosphate binders and vitamin D analogs, e.g., for the treatment of hyperparathyroidism. (Goel et al. (2011) "Treatment of Severe Metastatic Calcification and Calciphylaxis in Dialysis Patients," INTERNATIONAL JOURNAL OF NEPHROLOGY 2011:1-5.) Accordingly, in one aspect, the invention provides a disclosure of a method for preventing calciphylaxis in a subject or slowing the progression of, arresting, and/or reversing tissue calcification in a subject with calciphylaxis, wherein the subject is taking calcium-based phosphate binders and/or vitamin D analogs. The method can include administering to the subject at least 2 mg of substantially pure menaquinone-7 (MK-7) and/or menaquinol-7 (MKH2-7) per day. In certain embodiments, the subject has hyperparathyroidism.

Examples of calcium-based phosphate binders include calcium carbonate and calcium acetate. Examples of vitamin D analogs include calcitrol, alfacalcidol, paricalcitol, maxacalcitol, and 2-methylene-19-nor-(20S)-1α, 25(OH)$_2$D$_3$ (2MD).

IV. Biomarkers Useful for Determining Prevention, Slowing the Progression of, Arresting, and/or Reversing, Calciphylaxis in a Subject In certain embodiments, biomarkers can be assessed to determine whether the methods and/or compositions described herein are effective at preventing or treating (e.g., slowing the progression of, arresting, and/or reversing) calciphylaxis in a subject. These include, for example, measuring a subject's T50 times and measuring a ratio of carboxylated Vitamin K-dependent proteins to non-carboxylated proteins, as described in more detail below.

1. Primary Calciprotein Particles (CPPs) and Serum T50

Under normal physiologic conditions, pathological calcification is prevented in part by primary calciprotein particles (CPPs) (Price, et al., supra). CPPs comprise circulating calcium phosphate crystals complexed with two calcification inhibiting proteins, Fetuin A and Matrix Gla Protein. (Id.) Matrix Gla Protein is a Vitamin K-dependent protein and formation of CPPs is dependent upon the gamma carboxylation of Matrix Gla Protein. (Id.) Pre-clinical studies suggest that the calciprotein system functions as an alternative means for preventing pathologic calcification when humoral lines of defense such as pyrophosphate, magnesium and albumin are overwhelmed. The binding of calcium-phosphate crystals by primary CPPs occurs in a coordinated and time-dependent process.

The time necessary for 50% (T50) conversion of primary CPPs to secondary CPPs is an accurate and highly sensitive means for determining the capacity of plasma to sequester excess calcium phosphate crystals. The conversion from primary to secondary forms involves the formation of a more elongated crystal. The elongation leads to a more turbid solution which can be detected by nephelometry. Under conditions of heavy calcium phosphate burden, the time to reach 50% conversion is shortened to due reduced reserves for calcium phosphate absorption. Thus, short T50 times suggest a reduced capacity to absorb calcium phosphate crystals whereas prolonged T50 times are consistent with high capacities. Short T50 times are often associated with warfarin treatment, or hemodialysis or uremic oxidative load, and generally are associated with increased risk of myocardial infarctions, heart failure and all-cause mortality.

Without wishing to be bound by theory, it is believed that the administration of MK-7 and/or MKH2-7 increases T50 times and improving a subject's capacity to prevent pathologic calcification. Because subjects with CKD and ESRD exhibit reduced levels of carboxylated Matrix Gla Protein, which is Vitamin K-dependent and essential for the formation of primary CPP, administration of MK-7 and/or MKH2-7 in accordance with the methods of the present disclosure can reduce the risk for pathologic calcification and prevent the development of calciphylaxis.

Accordingly, in certain embodiments of the methods disclosed herein, administration of the MK-7 and/or MKH2-7 to the subject increases the subject's serum T50 value (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the subject's serum T50 value prior to administration of the MK-7 and/or MKH2-7. Methods for measuring a subject's serum T50 value are known in the art. (See, e.g., Pasch et al. (2012) "Nanoparticle-based test measures overall propensity for calcification in serum." J. AM. SOC. NEPHROL. 23(10): 1744-52; Dahle et al., (2016) "Serum Calcification Propensity Is a Strong and Independent Determinant of Cardiac and All-Cause Mortality in Kidney Transplant Recipients." AM. J. TRANSPLANT 16(1): 204-12; and Smith et al. (2014) "Serum Calcification Propensity Predicts All-Cause Mortality in Predialysis CKD," J. AM. SOC. NEPHROL. 25(2):339-348).

In certain embodiments, the disclosure relates to a method of increasing a serum T50 value in a subject having a disorder as described herein, the method comprising administering at least 2 mg/day (e.g., at least 2 mg of substantially pure MK-7 and/or MKH2-7 per day, e.g., 10, 15, 25, 50 or 75 mg per day) MK-7 and/or MKH2-7 to the subject, wherein administration of the MK-7 and/or MKH2-7 to the subject increases the subject's serum T50 value (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the subject's serum T50 value prior to administration of the MK-7 and/or MKH2-7.

2. Carboxylation of Vitamin K-Dependent Proteins

Despite dietary deficiencies, Vitamin K levels among ESRD patients may not be reduced. For example, a study of 172 stable hemodialysis patients found that only 6% of patients exhibited a clinically significant deficiency in Vitamin K. (Holden et al. (2010) "Vitamins K and D Status in Stages 3-5 Chronic Kidney Disease," CLIN. J. AM. SOC. NEPHROL. 5:590-597.) However, when patients were examined for the level of carboxylated osteocalcin, a Vitamin K-dependent protein, approximately 60% of patients had reduced levels. (Id.) Similar results were shown for other Vitamin K-dependent proteins, such as PIVKA-II. (Id., and Pilkey et al. (2007) "Subclinical Vitamin K Deficiency in Hemodialysis Patients," AM. J. KIDNEY DIS. 49:432-439.) These results are consistent with the hypothesis that in uremic patients, total Vitamin K levels can be normal while generation of reduced forms are blocked by the oxidative properties of uremia. (Id.)

The observation that oxidant conditions can disrupt the Vitamin K cycle suggests that the oxidant load generated during hemodialysis further contributes to the high rates of soft tissue (e.g., vascular) calcification observed within the ESRD population. Delivery of hemodialysis is known to lead to the oxidation of numerous tissue proteins, and both CKD and ESRD patients exhibit a higher percentage (15-fold) of carbonyl proteins compared to normal controls.

Without wishing to be bound by the theory, it is believed that the oxidative load generated by uremia and/or hemodialysis leads to oxidation of the functional Vitamin K hydroquinone (KH2) to the non-functional native vitamin. The oxidation of KH2 blocks its ability to function as a co-factor for GGCX which leads to reduced gamma carboxylation of Vitamin K-dependent proteins. Thus, administration of MK-7 and/or MKH2-7 to subjects with diabetes, CKD, and/or ESRD and/or subjects undergoing hemodialysis, can increase the ratio of one or more carboxylated Vitamin K-dependent proteins to non-carboxylated Vitamin K-dependent proteins in these subjects and/or decrease the amount of one or more non-carboxylated Vitamin K-dependent proteins in these subjects.

Accordingly, in certain embodiments, administration of MK-7 and/or MKH2-7 increases a ratio of a carboxylated to a non-carboxylated Vitamin K-dependent protein in the subject's plasma (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the ratio prior to administration of the MK-7 and/or MKH2-7. In certain embodiments, administration of MK-7 and/or MKH2-7 increases a ratio of a carboxylated to a non-carboxylated Vitamin K-dependent protein in the subject's plasma by between about 10% and 500% or higher, between about 30% and about 500%, between about 30% and about 200%, between about 30% and about 100%. In certain embodiments, administration of MK-7 and/or MKH2-7 increases a ratio of a carboxylated to a non-carboxylated Vitamin K-dependent protein in the subject's plasma by between about 50% and about 500%, between about 50% and about 200%, between about 50% and about 100%. In certain embodiments, administration of MK-7 and/or MKH2-7 increases a ratio of a carboxylated to a non-carboxylated Vitamin K-dependent protein in the subject's plasma by between about 70% and about 500%, between about 70% and about 200%, between about 70% and about 100%.

In certain embodiments, administration of MK-7 and/or MKH2-7 reduces an amount of non-carboxylated Vitamin K-dependent protein in the subject's plasma (e.g., by at least 5%, 10%, 20%, 25%, 30%, 35%, 40%, 45%, 50%, 55%, 60%, 65%, 70%, 75%, 80%, 85%, 90%, 95%, or 100%) relative to the amount prior to administration of the MK-7 and/or MKH2-7. In certain embodiments, administration of MK-7 and/or MKH2-7 reduces an amount of a non-carboxylated Vitamin K-dependent protein in the subject's plasma by between about 5% and about 100%, between about 5% and about 80%, between about 5% and about 30%, between about 20% and about 100%, or between about 20% and about 100%.

In certain embodiments, the disclosure relates to a method for increasing a ratio of a carboxylated to a non-carboxylated Vitamin K-dependent protein in the plasma of a subject having a disorder as described herein, the method comprising administering at least 2 mg/day (e.g., at least 2 mg of substantially pure MK-7 and/or MKH2-7 per day, e.g., 10, 15, 25, 50 or 75 mg per day) MK-7 and/or MKH2-7 to the subject, wherein administration of the MK-7 and/or MKH2-7 to the subject increases a ratio of a carboxylated to a non-carboxylated Vitamin K-dependent protein in the subject's plasma (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the ratio prior to administration of the MK-7 and/or MKH2-7.

In certain embodiments, the disclosure relates to a method for decreasing an amount of a non-carboxylated Vitamin K-dependent protein in the plasma of a subject having a disorder as described herein, the method comprising administering at least 2 mg/day (e.g., at least 2 mg of substantially pure MK-7 and/or MKH2-7 per day, e.g., 10, 15, 25, 50 or 75 mg per day) MK-7 and/or MKH2-7 to the subject, wherein administration of the MK-7 and/or MKH2-7 to the subject decreases an amount of a non-carboxylated Vitamin K-dependent protein in the subject's plasma (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the amount prior to administration of the MK-7 and/or MKH2-7.

In certain embodiments, the Vitamin K-dependent protein is selected from Matrix Gla Protein (MGP), Growth Arrest Specific Gene 6 (Gas-6) protein, PIVKA-II protein, osteocalcin, activated Protein C, or activated Protein S. Carboxylated forms of MGP, Gas-6, PIVKA-II, osteocalcin, activated Protein C and activated Protein S can be measured using sandwich assays, as is known in the art. (See, e.g., Nigwekar et al. (2017), supra (detecting MGP); Gla-Type Osteocalcin (GLa-OC) ELISA Kit (Takara, Mountain View, Calif.); STA-Staclot Protein C (Stago, Asnieres sur Seine, France; and REAADS Protein S Antigen, cat. no. K036-001, Diapharma Group, West Chester, Ohio). An increase in the ratio of carboxylated to non-carboxylated Vitamin K-dependent proteins in a subject following administration with MK-7 is indicative of successful rescue of the GGCX carboxylation system. Accordingly, effective MK-7 and/or MKH2-7 administration can lead to an increase in the ratio of carboxylated to non-carboxylated proteins in the subject.

PIVKA-II is an abnormal form of prothrombin which has not been carboxylated, also known as des-gamma carboxyprothrombin (DCP). Thus, elevated levels of PIVKA-II correspond to poorer vitamin K status. As a biomarker of vitamin K status, PIVKA-II has the advantage of being independent of kidney function and lipid profile (Elliot et al. (2014) "Assessment of potential biomarkers of subclinical vitamin K deficiency in patients with end-stage kidney disease," CAN. J. KIDNEY HEALTH DIS. 1:13.) According to the methods herein, measuring PIVKA-II in a subject is indicative of successful rescue of the GGCX carboxylation system. PIVKA-II plasma levels can be measured by any method known in the art, e.g., using ELISA (Diagnostica Stage, Parsippany, N.J.). (See also, e.g., Dituri et al. (2012) "PIVKA-II plasma levels as markers of subclinical vitamin K deficiency in term infants," J. MATERNAL-FETAL & NEONATAL MEDICINE 25(9): 1660-1663.)

MGP is believed to be a potent calcification inhibitor of the arterial wall and other soft tissues, where its activity depends on vitamin K-dependent γ-glutamate carboxylation (Schurgers et al. (2007a), supra; Westenfeld et al. (2012) "Effect of vitamin K2 supplementation on functional vitamin K deficiency in hemodialysis patients: a randomized trial," AM. J. KIDNEY DIS. 59(2):186-195; Schurgers et al. (2013) "Vitamin K-dependent carboxylation of matrix Gla-protein: a crucial switch to control ectopic mineralization," TRENDS MOL MED 2013; 19(4):217-26; Marles et al. (2017) "US Pharmacopeial Convention safety evaluation of menaquinone-7, a form of vitamin K," NUTR. REV. 75(7): 553-578). Uncarboxylated MGP, formed as a result of vitamin K deficiency, is associated with cardiovascular disease. Recent studies suggest poor vitamin K status in hemodialysis patients (Westenfeld et al. (2012), supra). The circulating inactive form of MGP (dp-ucMGP) was shown to increase progressively in patients with CKD (Schurgers et al. (2010), supra) and to be predictive of vitamin K status and correlated with vascular calcification in patients on hemodialysis (Delanaye et al. (2014), supra). Plasma dp-ucMGP has therefore been proposed as a surrogate marker for vascular calcification in CKD (Schurgers et al. (2010), supra). In addition, lower levels of circulating desphospho-carboxylated MGP (dp-cMGP) was proposed as a predictor of mortality in hemodialysis patients (Schlieper et al. (2011) "Circulating nonphosphorylated carboxylated matrix gla protein predicts survival in ESRD," J. AM. SOC. NEPHROL. 22(2):387-95).

Osteocalcin is a non-collagenous bone matrix protein synthesized by mature osteoblasts, and involved in bone formation and re-gelation of bone mineralization (Elliott et al. 2014, supra; Marles et al. 2017, supra). The proportion of osteocalcin that is uncarboxylated is a sensitive marker of vitamin K status in bone, and subclinical vitamin K deficiency is defined by an increase in the proportion of uncarboxylated osteocalcin above 20% (Elliott et al. 2014, supra). Supplementation with MK-7 at doses of 100-200 μg/d for 4 to 12 weeks was shown to increase the ratio of carboxylated to undercarboxylated osteocalcin significantly and in a dose-dependent manner (Inaba et al. (2015), "Low-Dose Daily Intake of Vitamin K(2) (Menaquinone-7) Improves Osteocalcin γ-Carboxylation: A Double-Blind, Randomized Controlled Trials," J. NUTR. SCI. VITAMINOL. 61(6):471-80).

Vitamin K-dependent γ-carboxyglutamate proteins are synthesized in the liver, and help maintain normal blood coagulation through a balance of both procoagulant factors (II, VII, IX, and X) and anticoagulant proteins (C and S) (Schurgers et al. (2007c) "Vitamin K-containing dietary supplements: comparison of synthetic vitamin K1 and natto-derived menaquinone-7," BLOOD 109(8):3279-83; Marles et al. (2017) supra). Protein C regulates the coagulation process by neutralizing the procoagulant activities of factors V and VIII in the presence of the cofactor Protein S (Marlar et al. (2017) "Assessment of Hereditary Thrombophilia: Performance of Protein C (PC) Testing," METHODS MOL. BIOL. 1646:145-151). Hypercoagulable states, such as protein C and/or protein S deficiencies, have been reported in patients with calciphylaxis, and proposed as factors increasing the likelihood of calciphylaxis development (Wilmer et al. (2002), supra; Nigwekar et al. (2008) "Calciphylaxis from nonuremic causes: a systematic review," CLIN. J. AM. SOC. NEPHROL. 3(4):1139-43). In a randomized study evaluating the effect of vitamin K2 supplementation on functional vitamin K deficiency in adult hemodialysis patients, patients on hemolysis (N=53) had 4.5-fold higher dp-ucMGP and 8.4-fold higher uncarboxylated osteocalcin levels compared with healthy age-matched controls (N=50). PIVKA-II levels were elevated in 49 hemodialysis patients. Vitamin K2 supplementation induced a close- and time-dependent decrease in circulating dp-ucMGP, uncarboxylated osteocalcin, and PIVKA-II levels. Response rates in the reduction in dp-ucMGP levels were 77% and 93% in the groups receiving 135 μg and 360 μg of menaquinone-7, respectively (Westenfeld et al. (2012) supra).

3. Levels of Other Biomarkers for Calcification

In certain embodiments, administration of the MK-7 and/or MKH2-7 increases the plasma level of osteoprotegerin or Fetuin A (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the plasma concentration of osteoprotegerin or Fetuin A prior to administration of the MK-7 and/or MKH2-7. In certain embodiments, administration of the MK-7 and/or MKH2-7 increases the plasma level of osteoprotegerin or Fetuin A by about 10-50%, by about 50-100%, by about 100-200%, or by about 200-500% relative to the plasma concentration of osteoprotegerin or Fetuin A prior to administration of the MK-7 and/or MKH2-7. Osteoprotegerin and Fetuin A are inhibitors of tissue calcification. Accordingly, an increase in levels of osteoprotegerin and/or Fetuin A is indicative that administration of the MK-7 and/or MKH2-7 is successfully preventing, slowing the progression of, arresting, and/or reversing calciphylaxis.

In certain embodiments, the disclosure relates to a method for increasing the plasma level of osteoprotegerin or Fetuin A in a subject having a disorder as described herein, the method including administering at least 2 mg/day (e.g., at least 2 mg of substantially pure MK-7 and/or MKH2-7 per day, e.g., 10, 15, 25, 50 or 75 mg per day) MK-7 and/or MKH2-7 to the subject, wherein administration of the MK-7 and/or MKH2-7 to the subject increases the plasma level of osteoprotegerin or Fetuin A (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the plasma concentration of osteoprotegerin or Fetuin A prior to administration of the MK-7 and/or MKH2-7.

In certain embodiments of any of the above aspects, administration of the MK-7 and/or MKH2-7 decreases the plasma level of D-Dimers (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the plasma concentration of D-Dimers prior to administration of the MK-7 and/or MKH2-7. In certain embodiments of any of the above aspects, administration of the MK-7 and/or MKH2-7 decreases the plasma level of D-Dimers by about 10-50%, by about 50-100%, or by about 10-100% relative to the plasma concentration of D-Dimers prior to administration of the MK-7 and/or MKH2-7. D-Dimers are indicative of the functional status of Vitamin D metabolism. Protein C and Protein S prevent generation of thrombin and fibrin, and the lack of functional Vitamin K contributes to a loss of Protein C and Protein S, which can lead to microthrombosis via degradation of fibrin and formation of D-Dimers. Thus presence of D-Dimers is an indicator of sub-clinical thrombosis. Accordingly, reduction in the plasma level of D-Dimer may indicate that administration of the MK-7 and/or MKH2-7 is successfully restoring the GGCX carboxylation system, which can lead to preventing, slowing the progression of, arresting, and/or reversing calciphylaxis.

In certain embodiments, the disclosure relates to a method for decreasing the plasma level of D-Dimers in a subject having a disorder as described herein, the method including administering at least 2 mg/day (e.g., at least 2 mg of substantially pure MK-7 and/or MKH2-7 per day, e.g., 10, 15, 25, 50 or 75 mg per day) MK-7 and/or MKH2-7 to the subject, wherein administration of the MK-7 and/or MKH2-7 to the subject decreases the plasma level of D-Dimers (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the plasma concentration of D-Dimers prior to administration of the MK-7 and/or MKH2-7.

In certain embodiments of any of the above aspects, administration of the MK-7 and/or MKH2-7 decreases the plasma level of Highly Sensitive C Reactive Protein (hs-CRP) (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the plasma concentration of Highly Sensitive C Reactive Protein (hs-CRP) prior to administration of the MK-7 and/or MKH2-7. In certain embodiments of any of the above aspects, administration of the MK-7 and/or MKH2-7 decreases the plasma level of Highly Sensitive C Reactive Protein (hs-CRP) by about 10-50%, by about 50-100%, or by about 10-100% relative to the plasma concentration of Highly Sensitive C Reactive Protein (hs-CRP) prior to administration of the MK-7 and/or MKH2-7. Hs-CRP is a biomarker for ongoing inflammation. The presence of inflammation enhances calciphylaxis. Accordingly, reduction in the plasma level of hs-CRP can be indicative that administration of the MK-7 and/or MKH2-7 is successfully preventing, slowing the progression of, arresting, and/or reversing calciphylaxis.

In certain embodiments, the disclosure relates to a method for decreasing the plasma level of Highly Sensitive C Reactive Protein (hs-CRP) in a subject having a disorder as described herein, the method including administering at least 2 mg/day (e.g., at least 2 mg of substantially pure MK-7 and/or MKH2-7 per day, e.g., 10, 15, 25, 50 or 75 mg per day) MK-7 and/or MKH2-7 to the subject, wherein administration of the MK-7 and/or MKH2-7 to the subject decreases the plasma level of Highly Sensitive C Reactive Protein (hs-CRP) (e.g., by at least 5%, 10%, 15%, 20%, 25%, 30%, 35%, 40%, 45% 50%, 55%, 60%, 65%, 70%, 75%, 80%, 85%, 90%, 95%, or 100%) relative to the plasma concentration of Highly Sensitive C Reactive Protein (hs-CRP) prior to administration of the MK-7 and/or MKH2-7.

V. Lesions

The methods and compositions described herein can be useful in arresting or stopping the progression of, or reversing tissue lesions, for example dermal lesions or vascular lesions.

1. Dermal Lesions

The final step of the Vitamin K cycle requires the enzymatic reduction of Vitamin K 2,3-epoxide back to MK-7 by Vitamin K epoxide reductase complex subunit 1 (VKORC1, also referred to as VKOR (see, FIG. 1). In some tissues, the paralog VKORC1L1 (VKORC1-Like-1) may also perform the reaction. Skin exhibits the lowest expression of VKOR-C1, consistent with the clinical observation that Vitamin K-dependent vascular calcification is more common in the dermis. Low skin expression of VKOR-C1 also suggests that any condition or procedure that blocks the generation of Vitamin K, such as hemodialysis, predisposes skin to pathologic calcification.

Thus, the methods and compositions described herein relate in part to reducing the size of a dermal lesion. In certain embodiments, the subject has a dermal lesion, and the administration of the MK-7 and/or MKH2-7 reduces the size of the dermal lesion. In certain embodiments, administration of the MK-7 and/or MKH2-7 reduces the total surface area of the dermal lesion by at least 55%, 10%, 15%, 20%, 25%, 30%, 35%, 40%, 45% 50%, 55%, 60%, 65%, 70%, 75%, 80%, 85%, 90%, 95%, or 100%. In certain embodiments, administration of the MK-7 and/or MKH2-7 reduces the total volume of the dermal lesion by at least 5%, 10%, 15%, 20%, 25%, 30%, 35%, 40%, 45% 50%, 55%, 60%, 65%, 70%, 75%, 80%, 85%, 90%, 95%, or 100% (i.e., the dermal lesion is eliminated).

In certain embodiments, administration of MK-7 and/or MKH2-7 reduces the total surface area or volume of the dermal lesion by between about 30% and about 100%, between about 30% and about 90%, between about 30% and about 80%, between about 30% and about 70%, or between about 30% and about 60%. In certain embodiments, administration of MK-7 and/or MKH2-7 reduces the total surface area or volume of the dermal lesion by between about 50% and about 100%, between about 50% and about 90%, between about 50% and about 80%, between about 50% and about 70%, or between about 50% and about 60%. In certain embodiments, administration of MK-7 and/or MKH2-7 reduces the total surface area or volume of the dermal lesion by between about 70% and about 100%, between about 70% and about 90%, between about 70% and about 80%.

The surface area or volume of one or more skin lesions can be measured by any method known in the art. When surface area is measured, a mean total surface area can be calculated if multiple lesions are present. Volume of a lesion can be calculated from a three-dimensional model of the lesion which is constructed from digital imaging.

Further, prior to the development of outward signs of a dermal lesion, the size of the dermal lesion can be measured by digital analysis. In another embodiment, the effectiveness of administration of MK-7 and/or MKH2-7 is determined by Von Kossa staining for calcium in a dermal biopsy. This well-established stain is a validated means to examine and quantify the amount of interstitial calcium deposition in a dermal biopsy. In this approach, a skin biopsy is taken and the tissue is stained using the Von Kossa method. By binding to soft tissue and vascular deposits of phosphate, Von Kossa staining can be used to determine whether the rate of soft tissue and vascular calcium phosphate deposition is being slowed or reversed with administration of MK-7 and/or MKH2-7. Because the calcium phosphate deposits are central to pathogenesis of calciphylaxis, a reduction in Von Kossa staining indicates a healing of the conditions that lead to calciphylaxis lesions. Kits for performing the Von Kossa method are available commercially (see, e.g., Abcam®, #ab150687).

In certain embodiments, administration of the MK-7 and/or MKH2-7 reduces the dermal lesion to 95%, 90%, 85%, 80%, 75%, 70%, 65%, 60%, 55%, 50%, 45%, 40%, 35%, 30%, 25%, 20%, 15%, 10%, 5%, or 0% (i.e., the dermal lesion is eliminated) of the total surface of the lesion prior to treatment.

2. Vascular Lesions

The methods and compositions described herein relate in part to reducing a vascular lesion. In certain embodiments, the subject has a vascular lesion, and the administration of the MK-7 and/or MKH2-7 reduces the vascular lesion. Reduction in a vascular lesion can be assessed using aortic plethysmography, which measures vascular compliance (i.e., the capacity of a blood vessel to dilate). (See, e.g., Inuma et al. (2012) HONG KONG JOURNAL OF NEPHROLOGY 14(2): 48-53.)

Reduction in a vascular lesion also can be assessed by measuring pulse wave velocity (PWV). PWV is the velocity at which the arterial pulse moves through the circulatory system and is used as a measure of arterial stiffness. Higher PWV corresponds to higher arterial stiffness, and therefore lower vascular compliance. Methods for measuring PWV are known in the art and described, for example, by Pereira et al. (2015), supra. Briefly, PWV can be assessed by measuring regional PWV, such as carotid-femoral PWV, or local PWV. Methods for measuring regional PWV are known in the art and include, for example, the use of a pulse transducer probe, TY-360 pressure transducer, doppler unit synchronism with electrocardiogram (ECG), pulse transducer probes, photoplethysmography, Complior® (piezoelectric pressure transducers), SphygmoCor®, Arteriograph®, and PulsePen® (tonometer and integrated electrocardiogram unit). Id. Methods for measuring local PWV are known in the art and include, for example, magnetic resonance imaging, ultrasound, and angiography. Id.

In certain embodiments, administration of the MK-7 and/or MKH2-7 increases vascular compliance of a blood vessel by at least 5%, 10%, 15%, 20%, 25%, 30%, 35%, 40%, 45% 50%, 55%, 60%, 65%, 70%, 75%, 80%, 85%, 90%, 95%, or 100% relative to vascular compliance prior to treatment. In certain embodiments, administration of the MK-7 and/or MKH2-7 increases vascular compliance of a blood vessel by about 10-50%, by about 50-100%, by about 100-200%, or by about 200-500%. In certain embodiments, administration of the MK-7 and/or MKH2-7 increases vascular compliance of a blood vessel by at least 5%, 10%, 15%, 20%, 25%, 30%, 35%, 40%, 45% 50%, 55%, 60%, 65%, 70%, 75%, 80%, 85%, 90%, 95%, or 100% relative to vascular compliance prior to treatment. In certain embodiments, administration of the MK-7 and/or MKH2-7 increases vascular compliance of a blood vessel by about 10-50%, by about 50-100%, by about 100-200%, or by about 200-500% relative to vascular compliance prior to treatment.

VI. Kits for Use in Medical Applications

Another aspect of the invention provides a kit for treating one or more of the disorders or conditions described herein. The kit can include: i) instructions for treating the medical disorder; and ii) one or more dosage units containing substantially pure MK-7 and/or MKH2-7.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

Unless defined otherwise, all technical and scientific terms used herein have the same meaning as commonly understood by one of ordinary skill in the art to which this invention belongs.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also include the specific quantitative value itself, unless specifically stated otherwise. As used herein, the term "about" refers to a ±10% variation from the nominal value unless otherwise indicated or inferred.

Where a molecular weight is provided and not an absolute value, for example, of a polymer, then the molecular weight should be understood to be an average molecule weight, unless otherwise stated or understood from the context.

As a general matter, compositions specifying a percentage are by weight unless otherwise specified. Further, if a variable is not accompanied by a definition, then the previous definition of the variable controls.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby.

Example 1—Administration of MK-7 and/or MKH2-7 in Subjects at Risk for Development of Calciphylaxis This example describes the administration of MK-7 and/or MKH2-7 to subjects at risk for development of calciphylaxis, but who have not yet developed the characteristic skin lesions of calciphylaxis. Risk factors to be considered include, but are not limited to, diabetes mellitus, obesity, ESRD and/or hemodialysis, and prior treatment with warfarin (Nigwekar et al. (2016), supra). It is contemplated that administration of MK-7 and/or MKH2-7 can result in protection of the subjects from skin lesions and a change in certain biomarker levels indicative of the prevention of the development of calciphylaxis.

Subjects at risk of development of calciphylaxis orally receive MK-7 and/or MKH2-7 at 10 mg, 25 mg or 50 mg once daily for at least 2 weeks, 4 weeks, 6 weeks, 8 weeks, 3 months, 6 months, 1 year, or indefinitely. The dosage form is a 10 mg or 25 mg soft-gel capsule. Two 25 mg capsules are be administered once daily to the 50 mg dosage cohort.

It should be noted that not all subjects with elevated risk factors for calciphylaxis will develop the characteristic skin lesions of calciphylaxis. The intent of treating with MK-7 and/or MKH2-7 proactively (prior to a clinical diagnosis of calciphylaxis) is the prevention of lesion appearance. Thus, a drop in frequency of, or elimination of lesion appearances is contemplated to be a successful treatment.

Several biomarkers can be assessed to determine the efficacy of MK-7 and/or MKH2-7 at the three dose levels. Exemplary biomarkers include PIVKA-II; uncarboxylated and total Matrix Gla Protein (MGP); uncarboxylated, carboxylated and total osteocalcin protein; uncarboxylated, carboxylated and total Protein C, osteoprotegerin, Fetuin A and hs-CRP.

Blood samples are obtained to measure the biomarkers according to the following schedule. Blood sampling can occur during treatment on a weekly or monthly basis. It is contemplated that administration of MK-7 and/or MKH2-7 will result in (i) an increase in PIVKA-II, osteoprotegerin, or Fetuin A, which is indicative of slowing the progression of, arresting, or reversing, calciphylaxis, (ii) a decrease in uncarboxylated MGP, uncarboxylated osteocalcin, and/or uncarboxylated Protein C, which is indicative of slowing the progression of, arresting, or reversing calciphylaxis.

Further, pulse wave velocity (PWV) can be measured to assess arterial compliance. Improved vascular compliance will be indicative of slowing the progression of, arresting, or reversing calciphylaxis.

Example 2—Administration of MK-7 and/or MKH2-7 in Subjects at Diagnosed with Calciphylaxis This example describes the administration of MK-7 and/or MKH2-7 to subjects diagnosed with calciphylaxis. Typical symptoms include presentation of characteristic painful skin lesions (Nigwekar et al. (2015) "Calciphylaxis: Risk Factors, Diagnosis, and Treatment." Am. J. Kidney Dis. 66:133-46). Definitive diagnosis of calciphylaxis is achieved via skin biopsy (Nigwekar, 2015 supra). Further conditions need to be considered for correct diagnosis (Id.).

Subjects diagnosed with calciphylaxis orally receive MK-7 and/or MKH2-7 at 10 mg, 25 mg or 50 mg once daily for at least 2 weeks, 4 weeks, 6 weeks, 8 weeks, 3 months, 6 months, 1 year, or indefinitely. The dosage form is a 10 mg or 25 mg soft-gel capsule. Two 25 mg capsules are administered once daily to the 50 mg dosage cohort.

The arrest of, or decreases in lesion size and frequency is contemplated to be an indication of successful treatment. It is contemplated that administration of MK-7 and/or MKH2-7 according to the foregoing will result in the arrest of, or decrease in lesion size and frequency.

Additionally, because calciphylaxis has a considerable mortality risk, increased overall survival time of diagnosed subjects will be an indication of treatment success. It is contemplated that administration of MK-7 and/or MKH2-7 according to the foregoing will result in an increased overall survival time of diagnosed subjects.

Example 3—Administration of MK-7 and/or MKH2-7 in Subjects with Stable End Stage Renal Disease (ESRD) Receiving Hemodialysis This example describes the administration of MK-7 to subjects with ESRD receiving hemodialysis, and who are at risk of developing calciphylaxis. Administration of MK-7 can result in a change in certain biomarker levels indicative of the prevention of the development of calciphylaxis, or in the arrest or slowing down of the development of calciphylaxis.

A number of subjects with stable ESRD but without calciphylaxis are enrolled in the study, whereupon the subjects orally receive a 10 mg capsule of MK-7 per day for 14 days. The levels of certain biomarkers, including uncarboxylated Matrix Gla Protein (MGP), uncarboxylated osteocalcin, osteoprotegerin, Fetuin A and hs-CRP were assessed on day 1 and on day 15 (the end of treatment), and the changes between day 1 and day 15 were calculated. Between days 1 and 15, the average reduction in uncarboxylated MGP was −21.9% and the average reduction in uncarboxylated osteocalcin was −55.5%. In addition, subjects unexpectedly exhibited an average increase in osteoprotegerin and Fetuin A and a reduction in hs-CRP. Osteoprotegerin, Fetuin A, and hs-CRP are not Vitamin-K dependent proteins and it is believed that changes in these proteins have not previously been demonstrated as a result of MK-7 intake. The average increase in osteoprotegerin was 14.5%, the average increase in Fetuin A was 23.1%, and the average reduction in hs-CRP was −35.8%.

Based on the study, the administration of MK-7 can result in a decrease in uncarboxylated MGP, uncarboxylated osteocalcin, and hs-CRP, and an increase in Fetuin A and osteoprotegerin, which can be indicative that administration of MK-7 prevents, or stops or slows down the progression of calciphylaxis in the subjects.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating calciphylaxis in a human subject in need thereof, the method comprising administering to the human subject (a) menaquinone-7 (MK-7) and/or menaquinol-7 (MKH2-7); and (b) a statin; whereupon the administration of the MK-7 and/or MKH2-7:
   (i) increases a plasma level of Fetuin A relative to the plasma level of Fetuin A prior to administration; or
   (ii) decreases a plasma level of Highly Sensitive C Reactive Protein (hs-CRP) relative to the plasma level of hs-CRP prior to administration.

2. The method of claim 1, wherein the statin is selected from simvastatin, lovastatin, atorvastatin, pravastatin, pitavastatin, rosuvastatin, and fluvastatin.

3. The method of claim 1, wherein from about 10 mg to about 50 mg of MK-7 and/or MKH2-7 is administered to the subject per day.

4. The method of claim 1, wherein 10, 25, 50, 75 or 100 mg of MK-7 and/or MKH2-7 is administered to the subject per day.

5. The method of claim 1, wherein the composition is administered to the subject for at least 2 weeks.

6. The method of claim 1, wherein the composition is administered daily.

7. The method of claim 1, wherein the composition is administered orally.

8. The method of claim 1, wherein the subject is taking calcium-based phosphate binders and/or vitamin D analogs.

9. The method of claim 1, wherein the MK-7 and/or MKH2-7 is administered in the same dosage form as the statin.

10. The method of claim 1, wherein the MK-7 and/or MKH2-7 is administered in a separate dosage form from the statin.

11. The method of claim 1, wherein the composition is administered to the subject for at least 6 weeks.

12. The method of claim 1, wherein the subject is diabetic.

13. The method of claim 12, wherein the subject is undergoing hemodialysis.

14. The method of claim 13, wherein the composition is administered to the subject for a period that includes the duration of hemodialysis.

15. The method of claim 1, wherein the composition is disposed within a tablet, caplet, or capsule.

16. The method of claim 1, wherein the composition comprises MK-7 and/or MKH2-7 and a pharmaceutically acceptable excipient.

17. The method of claim 1, wherein, prior to administration of the composition, the subject has a uremic oxidative blockade.

18. The method of claim 1, whereupon administration of the MK-7 and/or MKH2-7 to the subject increases the subject's serum T50 value relative to the subject's serum T50 value prior to administration of the MK-7 and/or MKH2-7.

19. The method of claim 1, wherein administration of the MK-7 and/or MKH2-7
   (a) increases a ratio of a carboxylated to a non-carboxylated of a Vitamin K dependent protein or
   (b) decreases an amount of a non-carboxylated Vitamin K dependent protein in plasma of the subject relative to the ratio or amount present prior to administration of the MK-7 and/or MKH2-7.

20. The method of claim 19, wherein the Vitamin K-dependent protein is selected from Matrix Gla Protein, Growth Arrest Specific Gene 6 (Gas-6) protein, PIVKA-II protein, osteocalcin, activated Protein C, or activated Protein S.

21. The method of claim 1, wherein administration of the MK-7 and/or MKH2-7 to the subject decreases a plasma level of D-Dimer relative to the plasma level of D-Dimer prior to administration of the MK-7 and/or MKH2-7.

22. The method of claim 1, wherein at least about 10 mg of MK-7 and/or MKH2-7 is administered to the subject per day.

23. The method of claim 1, wherein the MK-7 and/or MKH2-7 is substantially pure.

24. The method of claim 1, whereupon the administration of the MK-7 and/or MKH2-7 increases a plasma level of Fetuin A relative to the plasma level of Fetuin A prior to administration.

25. The method of claim 1, wherein at least about 10 mg of substantially pure MK-7 and/or MKH2-7 is administered to the subject per day, whereupon the administration of the MK-7 and/or MKH2-7 increases a plasma level of Fetuin A relative to the plasma level of Fetuin A prior to administration.

* * * * *